(12) United States Patent
Soled et al.

(10) Patent No.: US 10,017,448 B2
(45) Date of Patent: Jul. 10, 2018

(54) PROCESS FOR HYDROGENATION OF BENZENEPOLYCARBOXYLIC ACIDS AND DERIVATIVES THEREOF

(71) Applicants: Stuart L. Soled, Pittstown, NJ (US); Sabato Miseo, Pittstown, NJ (US); Joseph E. Baumgartner, Califon, NJ (US); Christine E. Kliewer, Clinton, NJ (US); Hans K. T. Goris, Zaventem (BE)

(72) Inventors: Stuart L. Soled, Pittstown, NJ (US); Sabato Miseo, Pittstown, NJ (US); Joseph E. Baumgartner, Califon, NJ (US); Christine E. Kliewer, Clinton, NJ (US); Hans K. T. Goris, Zaventem (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/511,975

(22) PCT Filed: Oct. 9, 2015

(86) PCT No.: PCT/EP2015/073488
§ 371 (c)(1),
(2) Date: Mar. 16, 2017

(87) PCT Pub. No.: WO2016/066410
PCT Pub. Date: May 6, 2016

(65) Prior Publication Data
US 2017/0291867 A1 Oct. 12, 2017

Related U.S. Application Data

(60) Provisional application No. 62/072,005, filed on Oct. 29, 2014.

(30) Foreign Application Priority Data

Jan. 13, 2015 (EP) ..................... 15151010

(51) Int. Cl.
*C07C 69/74* (2006.01)
*C07C 51/36* (2006.01)
*C07C 69/75* (2006.01)
*B01J 23/46* (2006.01)
*B01J 8/02* (2006.01)

(52) U.S. Cl.
CPC ............. *C07C 51/36* (2013.01); *B01J 8/0278* (2013.01); *B01J 23/462* (2013.01); *B01J 23/464* (2013.01); *C07C 69/75* (2013.01); *C07C 2601/16* (2017.05)

(58) Field of Classification Search
CPC ...... B01J 23/462; B01J 23/464; B01J 8/0278; B01J 21/08; B01J 2219/00033; B01J 8/02; C07C 67/303; C07C 69/75; C07C 2601/16; C07C 51/36; C07C 2601/14; Y02P 20/582
See application file for complete search history.

(56) References Cited

U.S. PATENT DOCUMENTS

| 7,595,420 B2 | 9/2009 | Schlosberg et al. |
| 2006/0166809 A1 | 7/2006 | Malek et al. |
| 2012/0296111 A1* | 11/2012 | Konigsmann ............ B01J 21/08 560/127 |

FOREIGN PATENT DOCUMENTS

| EP | 0 005 737 | 12/1979 |
| WO | 94/29261 | 12/1994 |

OTHER PUBLICATIONS

Soled et al., "Supported Metal Catalysts: Some Interesting New Leads in an Old Field", St. Sur. Sci & Cat. (Scientific Bases for the Preparation of Heterogeneous Catalysts), vol. 162, pp. 103-110 (2006).

* cited by examiner

Primary Examiner — Yevgeny Valenrod
Assistant Examiner — Blaine G Doletski
(74) Attorney, Agent, or Firm — Darryl M. Tyus

(57) ABSTRACT

A process for ring hydrogenation of a benzenepolycarboxylic acid or derivative thereof, includes contacting a feed stream comprising the acid or derivative thereof with a hydrogen containing gas in the presence of a catalyst under hydrogenation conditions to produce a hydrogenated product, wherein the catalyst contains rhodium and ruthenium.

16 Claims, 9 Drawing Sheets

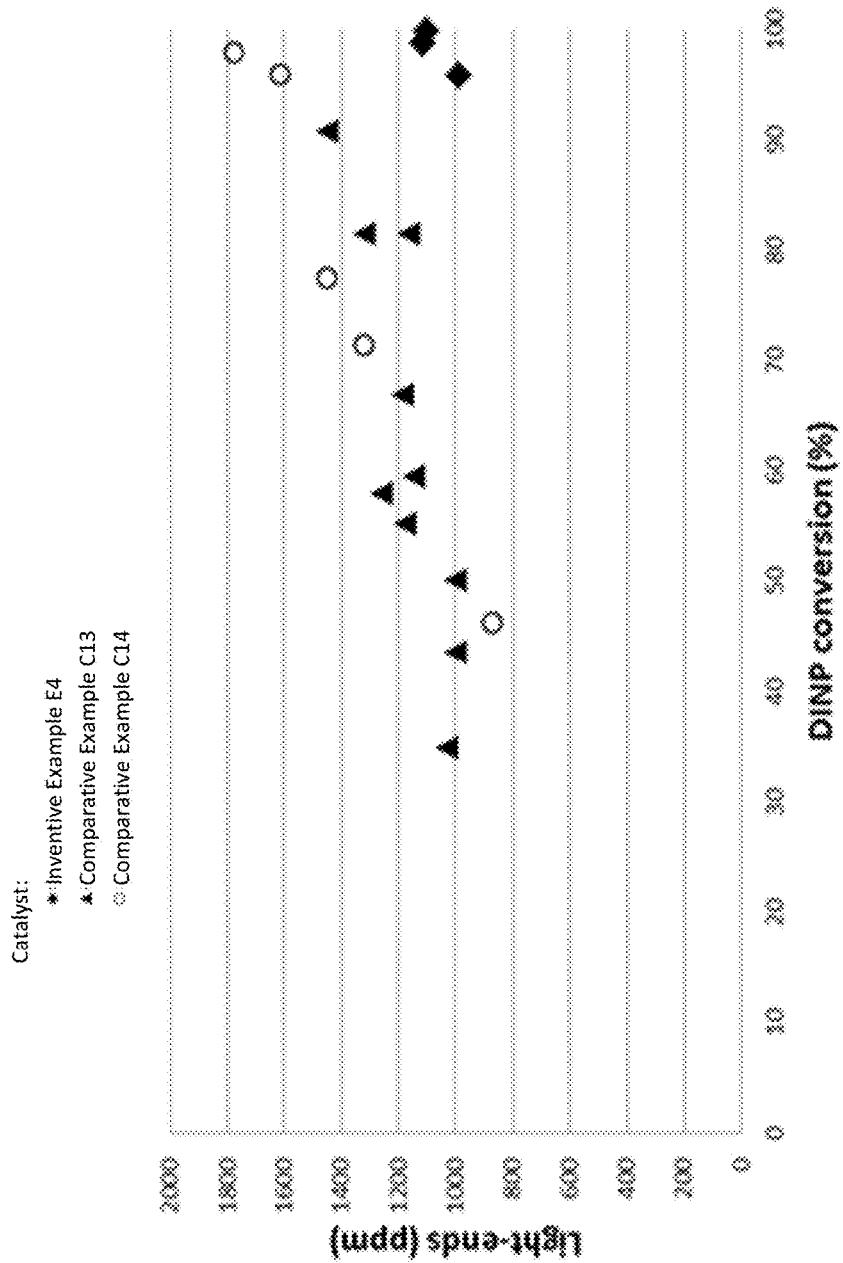

US 10,017,448 B2

PROCESS FOR HYDROGENATION OF BENZENEPOLYCARBOXYLIC ACIDS AND DERIVATIVES THEREOF

CROSS REFERENCE TO RELATION APPLICATIONS

This application is a National Stage Application under 35 USC 371 of International Application No. PCT/EP2015/073488, filed Oct. 9, 2015, which claims priority to and the benefits of U.S. patent application Ser. No. 62/072,005, filed Oct. 29, 2014, the disclosures of which are fully incorporated by reference in their entireties.

FIELD OF THE INVENTION

The present invention relates to a process for the hydrogenation of benzenepolycarboxylic acids and derivatives thereof, and to supported catalysts for the hydrogenation of benzenepolycarboxylic acids and derivatives thereof. More particularly, the present application relates to a process for the ring-hydrogenation of benzenepolycarboxylic acids and derivatives thereof utilizing a supported transition metal catalyst.

BACKGROUND OF THE INVENTION

Hydrogenation is an established process both in the chemical and petroleum refining industries. Hydrogenation is conventionally carried out in the presence of a catalyst, which usually comprises a metal hydrogenation component deposited on a porous support material. The metal hydrogenation component is often one or more metals, for example nickel, platinum, palladium, rhodium, ruthenium or mixtures thereof.

Many organic compounds have one or more groups or functionality that is susceptible to hydrogenation under appropriate conditions with the use of a suitable metal containing catalyst. One particular group of compounds that are susceptible to hydrogenation is those that contain one or more unsaturated groups or functionality such as for example carbon-carbon double bonds or triple bonds.

Hydrogenated derivatives of benzenepolycarboxylic acids or derivatives thereof, such as esters and/or anhydrides, have many uses. Of particular interest is their use as plasticisers for polymeric materials. In this context, the dialkylhexahydrophthalates are an example of one class of these compounds that are of particular interest. These materials may be produced by hydrogenation of the corresponding phthalic acid ester in the presence of a hydrogen-containing gas and an active metal hydrogenation catalyst deposited on a support.

Of particular importance in the hydrogenation of benzenepolycarboxylic acids or derivatives thereof is the degree of conversion of the starting materials and the selectivity of conversion into the desired hydrogenated cyclohexyl derivatives. The degree of conversion should be as high as possible and typically conversion levels of greater than 95% are sought and achieved for these types of hydrogenation. However, in these types of hydrogenation whilst high conversions may be obtained it is difficult to simultaneously achieve the required high degree of selectivity to the desired product. In this regard there is a problem with the generation of low molecular weight and/or boiling point by-products during the hydrogenation reaction. These by-products are often referred to as "lights" and they must be removed from the hydrogenation product before it is used, for example as a plasticiser.

The nature of the support material is often important to catalyst performance. Alumina is often used as a support in fields relating to petrochemical processing. However, it is sometimes preferable to use a nonacidic support, such as silica. U.S. Pat. No. 7,595,420 discloses a catalyst for hydrogenating benzenepolycarboxylic acids comprising platinum, palladium, ruthenium or mixtures thereof deposited on an ordered mesoporous support material having a high pore volume, a high surface area and controlled pore opening of at least 2 nm.

The arrangement of the metal on the support is also important. Metal particles should be small in size (i.e. the metal should be highly dispersed) and homogeneously distributed across the surface of the support. In order to maximize the number of available surface metal sites, the agglomeration of metal particles should be avoided.

A method of preparing supported metal catalysts is by reduction of a supported metal oxide. A typical method of making a supported metal oxide is by incipient wetness impregnation of a support with solutions containing metal salts, followed by drying and calcination. However, the high mobility of ruthenium oxide on silica makes the preparation of silica-supported ruthenium catalysts more challenging than the preparation of other silica-supported metal catalysts. In particular, the calcination of silica-supported ruthenium metal salts often leads to agglomeration of ruthenium oxide particles and results in a poorly dispersed catalyst.

Soled et al., St. Sur. Sci. & Cat., 162, 103-110 (2006) and US Patent App. Pub. 2006/166809 disclose a method of preparing silica-supported ruthenium catalysts that avoids the formation of ruthenium oxide intermediates. The process utilizes an amino alcohol or amino acid ligand, preferably triethanolamine, as a bifunctional dispersion aid. It is believed that ruthenium (amino alcohol/amino acid) complexes form strongly interacting precursors with silica support materials because the ligands simultaneously coordinate with both the support and ruthenium. Once the ruthenium complexes are dispersed across the support, the high hydrogenolysis activity of ruthenium is utilized to reduce and hydrogenolyse the ligands which would otherwise block active sites on the metal. However, a limitation of the process is the high temperature required for the hydrogenolysis step, typically about 400° C. Not all hydrogenation reactors, for example heritage hydrogenation reactors, are capable of reaching such temperatures, and so a complex external treatment step is often required.

Silica-supported rhodium catalysts are typically more straightforward to prepare because rhodium oxides are less mobile on silica than ruthenium oxides. Typically, the low mobility of rhodium oxides permits calcination of the catalyst precursor to remove organic ligands without the risk of metal particle agglomeration, and so there is no requirement for a high temperature hydrogenolysis step. However, a disadvantage of rhodium catalysts is the high cost of rhodium metal.

There is a need, therefore, for new hydrogenation processes for the conversion of benzenepolycarboxylic acids or derivatives thereof to the corresponding ring-hydrogenated derivatives, which processes produce lower levels of "lights" by-products and thus, offer improved selectivity for the desired products. There is also a need for new, efficient and cost effective supported metal hydrogenation catalysts having good metal dispersion and which can be prepared in a simple manner. It is therefore, an object of the present invention to provide a process for hydrogenating benzenedicarboxylic esters or anhydrides, using specific catalysts, by means of which the corresponding hydrogenation products may be obtained with high levels of conversion and selectivity.

SUMMARY OF THE INVENTION

In the process of the present invention, it has been found that a catalyst comprising rhodium and ruthenium provides a useful new catalyst for the ring hydrogenation of benzene polycarboxylic acids or derivatives thereof. Surprisingly, bimetallic rhodium-ruthenium solutions applied to a support material, for example silica, form well dispersed, small crystallites on the support which do not agglomerate when subjected to calcination. Unexpectedly, a process for ring hydrogenation of benzenepolycarboxlyic acids and derivatives thereof utilizing a supported catalyst comprising rhodium and ruthenium produces less lights by-product than a supported catalyst comprising ruthenium and not rhodium.

The present invention therefore provides a process for ring hydrogenation of a benzenepolycarboxylic acid or derivative thereof, which process comprises contacting a feed stream comprising said acid or derivative thereof with a hydrogen containing gas in the presence of a catalyst under hydrogenation conditions to produce a hydrogenated product, wherein said catalyst comprises rhodium and ruthenium, applied to a support material. Preferably the support is a silica support comprising from 97 to 100 wt % silica.

BRIEF DESCRIPTION OF THE DRAWINGS

FIG. 9 shows a graph of DINP conversion (%) against light ends content (ppm) for the catalytic tests of Example 8.

DETAILED DESCRIPTION OF THE INVENTION

Figure 1:
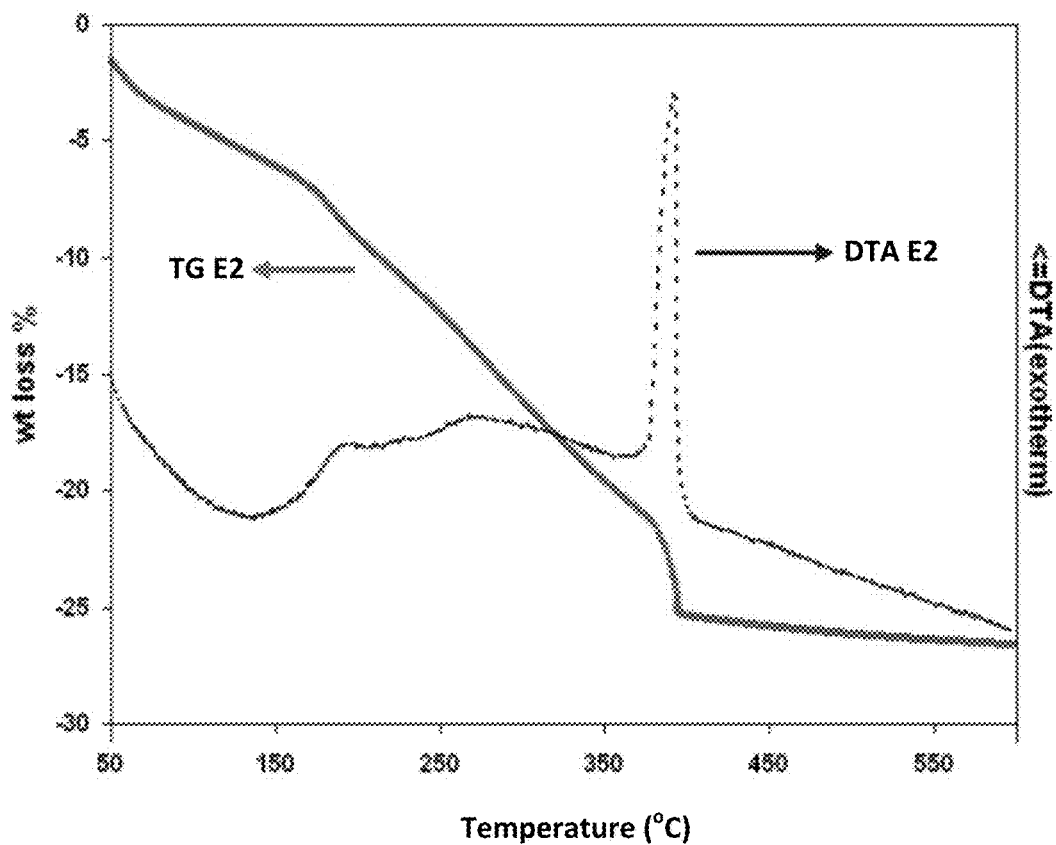
FIG. 1 shows a TG/DTA graph for example catalyst sample E2.

In the process of the present invention benzenepolycarboxylic acids or derivatives thereof are hydrogenated to the corresponding cyclohexyl derivative in the presence of a hydrogen-containing gas under hydrogenation conditions, wherein said catalyst comprises rhodium and ruthenium. It has been found that a catalyst comprising rhodium and ruthenium provides a highly active and efficient catalyst for the hydrogenation of benzenepolycarboxylic acids and derivatives thereof. In particular, it has been found that bimetallic ruthenium-rhodium catalysts show surprising, unanticipated behavior in the formation of small crystallites on catalyst support materials, for example non-acidic support materials, preferably silica.

Surprisingly, the bimetallic ruthenium-rhodium catalyst of the process of the invention shows higher activity in the ring hydrogenation of benzenepolycarboxylic acids and derivatives thereof, for example in the ring hydrogenation of dialkyl phthalates and dialkyl terephthalates, and a lower production of lights than the corresponding monometallic ruthenium catalyst. Furthermore, an advantage of the process of the invention is that the highly active bimetallic ruthenium-rhodium catalyst is less costly to produce than the corresponding monometallic rhodium catalyst because of the lower cost of ruthenium metal. In particular, a bimetallic ruthenium-rhodium catalyst comprising less rhodium by weight based on the total weight of the catalyst than the corresponding monometallic rhodium catalyst maintains activity comparable to or higher than the monometallic rhodium catalyst. In the foregoing, the term "corresponding monometallic catalyst" means a monometallic catalyst having the same support material as the bimetallic catalyst, and having a metal content in wt % equivalent to the combined ruthenium wt % and rhodium wt % of the bimetallic catalyst. For example, the monometallic ruthenium catalyst corresponding to a bimetallic ruthenium-rhodium catalyst comprising 0.5 wt % ruthenium and 0.5 wt % rhodium, based on the total weight of the catalyst, would have a ruthenium content of 1 wt %, based on the total weight of the catalyst.

Unexpectedly, it has been found that calcination of a supported bimetallic ruthenium-rhodium catalyst precursor does not result in agglomeration of the rhodium metal or of the ruthenium metal. Calcination of bimetallic ruthenium-rhodium catalyst supported on silica provides high dispersion of the ruthenium and rhodium metals, in particular when the calcination is carried out at a temperature within a range of from 350 to 500° C., preferably from 400 to 450° C. That finding contrasts with the behavior of the corresponding monometallic ruthenium catalyst precursor, which when subjected to calcination provides a catalyst having poor dispersion. It has been found that subjecting supported bimetallic ruthenium-rhodium catalyst precursors to a calcination step followed by a low temperature reduction step provides a highly dispersed bimetallic ruthenium-rhodium catalyst. In particular, the preparation of the catalyst of the process of the present invention avoids the necessity for a high temperature reduction step, as required for the preparation of the corresponding monometallic ruthenium catalyst. For example, if the supported bimetallic ruthenium-rhodium catalyst is prepared by a process involving the treatment of the catalyst support with a solution of a ruthenium amino alcohol complex or a solution of a ruthenium amino alcohol complex, the organic fragment can be removed by calcination rather than by a high temperature reduction step without significantly reducing the dispersity of the ruthenium on the support. Preferably, the supported bimetallic ruthenium-rhodium catalyst precursor is reduced at low temperature in situ, that is, the supported bimetallic ruthenium-rhodium catalyst precursor is reduced in the hydrogenation reactor of the hydrogenation process, thereby dispensing with the complicated, costly external reduction step often required for the hydrogenolysis of the corresponding supported monometallic ruthenium catalyst precursor.

The term "benzenepolycarboxylic acid or a derivative thereof" used for the purposes of the present invention encompasses all benzenepolycarboxylic acids as such, e.g. phthalic acid, isophthalic acid, terephthalic acid, trimellitic acid, trimesic acid, hemimellitic acid and pyromellitic acid, and derivatives thereof, particularly monoesters, diesters and possibly triesters and tetraesters, in particular alkyl esters, and anhydrides such as phthalic anhydride or trimellitic anhydride or their esters. The esters used are alkyl, cycloalkyl and alkoxyalkyl esters, where the alkyl, cycloalkyl and alkoxyalkyl groups generally have from 1 to 30, preferably from 2 to 20 and particularly preferably from 3 to 18, carbon atoms and can be branched or linear. Preferably, the benzenepolycarboyxlic acid or derivative thereof is a C7-C13 dialkyl phthalate, or a C7-C13 dialkyl terephthalate, or a mixture thereof.

One class of suitable benzenepolycarboxylic acids or a derivatives thereof are the alkyl terephthalates such as monomethyl terephthalate, dimethyl terephthalate, diethyl terephthalate, di-n-propyl terephthalate, di-n-butyl terephthalate, di-tert-butyl terephthalate, diisobutyl terephthalate, monoglycol esters of terephthalic acid, diglycol esters of terephthalic acid, di-n-octyl terephthalate, diisooctyl terephthalate, mono-2-ethylhexyl terephthalate, di-2-ethylhexyl terephthalate, di-n-nonyl terephthalate, diisononyl terephthalate, di-n-decyl terephthalate, di-n-undecyl terephthalate, diisodecyl terephthalate, diisoundecyl terephthalate, diisododecyl terephthalate, di-n-octadecyl terephthalate, diisooctadecyl terephthalate, di-n-eicosyl terephthalate, ditridecyl terephthalate, diisotridecyl terephthalate, monocyclohexyl terephthalate and or dicyclohexyl terephthalate. Also suitable are derivates in which the alkyl groups of the ester groups are different alkyl groups. Mixtures of one or more alkyl terephthalates may be used.

Another suitable class are the alkyl phthalates such as monomethyl phthalate, dimethyl phthalate, diethyl phthalate, di-n-propyl phthalate, di-n-butyl phthalate, di-tert-butyl phthalate, diisobutyl phthalate, monoglycol esters of phthalic acid, diglycol esters of phthalic acid, di-n-octyl phthalate, diisooctyl phthalate, di-2-ethylhexyl phthalate, di-n-nonyl phthalate, diisononyl phthalate, di-n-decyl phthalate, diisodecyl phthalate, di-n-undecyl phthalate, di-isoundecyl phthalate, diisododecyl phthalate, di-n-octadecyl phthalate, diisooctadecyl phthalate, di-n-eicosyl phthalate, monocyclohexyl phthalate, dicyclohexyl phthalate, alkyl isophthalates such as monomethyl isophthalate, dimethyl isophthalate, diethyl isophthalate, di-n-propyl isophthalate, di-n-butyl isophthalate, di-tert-butyl isophthalate, diisobutyl isophthalate, monoglycol esters of isophthalic acid, diglycol esters of isophthalic acid, di-n-octyl isophthalate, diisooctyl isophthalate, di-2-ethylhexyl isophthalate, di-n-nonyl isophthalate, diisononyl isophthalate, di-n-decyl isophthalate, diisodecyl isophthalate, di-n-undecyl isophthalate, di-isoundecyl isophthalate, diisododecyl isophthalate, di-n-octadecyl isophthalate, diisooctadecyl isophthalate, di-n-eicosyl isophthalate, monocyclohexyl isophthalate and or dicyclohexyl isophthalate. Also suitable are derivates in which the alkyl groups of the ester groups are different alkyl groups. Mixtures of one or more alkyl phthalates or isophthalates may be used.

A further suitable class are the alkyl trimellitates such as monomethyl trimellitate, dimethyl trimellitate, diethyl trimellitate, di-n-propyl trimellitate, di-n-butyl trimellitate, di-tert-butyl trimellitate, diisobutyl trimellitate, the monoglycol ester of trimellitic acid, diglycol esters of trimellitic acid, di-n-octyl trimellitate, diisooctyl trimellitate, di-2-ethylhexyl trimellitate, di-n-nonyl trimellitate, diisononyl trimellitate, di-n-decyl trimellitate, diisodecyl trimellitate, di-n-undecyl trimellitate, di-isoundecyl trimellitate, diisododecyl trimellitate, di-n-octadecyl trimellitate, diisooctadecyl trimellitate, di-n-eicosyl trimellitate, monocyclohexyl trimellitate, dicyclohexyl trimellitate and trimethyl trimellitate, triethyl trimellitate, tri-n-propyl trimellitate, tri-n-butyl trimellitate, tri-tert-butyl trimellitate, triisobutyl trimellitate, triglycol esters of trimellitic acid, tri-n-octyl trimellitate, triisooctyl trimellitate, tri-2-ethylhexyl trimellitate, tri-n-nonyl trimellitate, tri-isononyl trimellitate, tri-n-decyl trimellitate, triisododecyl trimellitate, tri-n-undecyl trimellitate, tri-isoundecyl trimellitate, tri-isoundecyl trimellitate, tri-isoundecyl trimellitate, tri-n-octadecyl trimellitate, tri-n-eicosyl trimellitate and tricyclohexyl trimellitate. Also suitable are derivates in which the alkyl groups of the ester groups are different alkyl groups. Mixtures of one or more alkyl trimellitates may be used.

Also suitable are the alkyl trimesates such as monomethyl trimesate, dimethyl trimesate, diethyl trimesate, di-n-propyl trimesate, di-n-butyl trimesate, di-tert-butyl trimesate, diisobutyl trimesate, monoglycol esters of trimesic acid, diglycol esters of trimesic acid, di-n-octyl trimesate, diisooctyl trimesate, di-2-ethylhexyl trimesate, di-n-nonyl trimesate, diisononyl trimesate, di-n-decyl trimesate, diisodecyl trimesate, di-n-undecyl trimesate, di-isoundecyl trimesate, diisododecyl trimesate, di-n-octadecyl trimesate, diisooctadecyl trimesate, di-n-eicosyl trimesate, monocyclohexyl trimesate, dicyclohexyl trimesate, and also trimethyl trimesate, triethyl trimesate, tri-n-propyl trimesate, tri-n-butyl trimesate, tri-tert-butyl trimesate, triisobutyl trimesate, triglycol esters of trimesic acid, tri-n-octyl trimesate, triisooctyl trimesate, tri-2-ethyl-hexyl trimesate, tri-n-nonyl trimesate, tri-isononyl trimesate, tri-n-decyl trimesate, triisododecyl trimesate, tri-n-undecyl trimesate, tri-isoundecyl trimesate, triisododecyl trimesate, tri-n-octadecyl trimesate, triisooctadecyl trimesate, tri-n-eicosyl trimesate and tricyclohexyl trimesate. Also suitable are derivates in which the alkyl groups of the ester groups are different alkyl groups. Mixtures of one or more alkyl trimesates may be used.

A further suitable class are the alkyl hemimellitates such as monomethyl hemimellitate, dimethyl hemimellitate, diethyl hemimellitate, di-n-propyl hemimellitate, di-n-butyl hemimellitate, di-tert-butyl hemimellitate, diisobutyl hemimellitate, monoglycol esters of hemimellitic acid, diglycol esters of hemimellitic acid, di-n-octyl hemimellitate, diisooctyl hemimellitate, di-2-ethylhexyl hemimellitate, di-n-nonyl hemimellitate, diisononyl hemimellitate, di-n-decyl hemimellitate, diisodecyl hemimellitate, di-n-undecyl hemimellitate, di-isoundecyl hemimellitate, diisododecyl hemimellitate, di-n-octadecyl hemimellitate, diisooctadecyl hemimellitate, di-n-eicosyl hemimellitate, monocyclohexyl hemimellitate, dicyclohexyl hemimellitate, and also trimethyl hemimellitate, triethyl hemimellitate, tri-n-propyl hemimellitate, tri-n-butyl hemimellitate, tri-tert-butyl hemimellitate, triisobutyl hemimellitate, triglycol esters of hemimellitic acid, tri-n-octyl hemimellitate, triisooctyl hemimellitate, tri-2-ethylhexyl hemimellitate, tri-n-nonyl hemimellitate, tri-isononyl hemimellitate, tri-n-decyl hemimellitate, triisodecyl hemimellitate, tri-n-undecyl hemimellitate, tri-isoundecyl hemimellitate, triisododecyl hemimellitate, tri-n-octadecyl hemimellitate, triisooctadecyl hemimellitate, tri-n-eicosyl hemimellitate and tricyclohexyl hemimellitate. Also suitable are derivates in which the alkyl groups of the ester groups are different alkyl groups. Mixtures of one or more alkyl hemimellitates may be used.

Another suitable class are the alkyl pyromellitates such as monomethyl pyromellitate, dimethyl pyromellitate, diethyl pyromellitate, di-n-propyl pyromellitate, di-n-butyl pyromellitate, di-tert-butyl pyromellitate, diisobutyl pyromellitate, monoglycol esters of pyromellitic acid, diglycol esters of pyromellitic acid, di-n-octyl pyromellitate, diisooctyl pyromellitate, di-2-ethylhexyl pyromellitate, di-n-nonyl pyromellitate, diisononyl pyromellitate, di-n-decyl pyromellitate, diisodecyl pyromellitate, di-n-undecyl pyromellitate, di-isoundecyl pyromellitate, diisododecyl pyromellitate, di-n-octadecyl pyromellitate, diisooctadecyl pyromellitate, di-n-eicosyl pyromellitate, monocyclohexyl pyromellitate, trimethyl pyromellitate, triethyl pyromellitate, tri-n-propyl pyromellitate, tri-n-butyl pyromellitate, tri-tert-butyl pyromellitate, triisobutyl pyromellitate, triglycol esters of pyromellitic acid, tri-n-octyl pyromellitate, triisooctyl pyromellitate, tri-2-ethylhexyl pyromellitate, tri-n-nonyl pyromellitate, tri-isononyl pyromellitate, triisodecyl pyromellitate, tri-n-decyl pyromellitate, tri-n-undecyl pyromellitate, tri-isoundecyl pyromellitate, triisododecyl pyromellitate, tri-n-octadecyl pyromellitate, triisooctadecyl pyromellitate, tri-n-eicosyl pyromellitate, tricyclohexyl pyromellitate, and also tetramethyl pyromellitate, tetraethyl pyromellitate, tetra-n-propyl pyromellitate, tetra-n-butyl pyromellitate, tetra-tert-butyl pyromellitate, tetraisobutyl pyromellitate, tetraglycol esters of pyromellitic acid, tetra-n-octyl pyromellitate, tetraisooctyl pyromellitate, tetra-2-ethylhexyl pyromellitate, tetra-n-nonyl pyromellitate, tetraisododecyl pyromellitate, tetra-n-undecyl pyromellitate, tetraisododecyl pyromellitate, tetra-n-octadecyl pyromellitate, tetraisooctadecyl pyromellitate, tetra-n-eicosyl pyromellitate, tetracyclohexyl pyromellitate. Also suitable are derivates in which the alkyl groups of the ester groups are different alkyl groups. Mixtures of one or more alkyl pyromellitates may be used.

Also suitable are anhydrides of phthalic acid, trimellitic acid, hemimellitic acid and pyromellitic acid.

Also suitable are alkyl terephthalates, alkyl phthalates, alkyl isophthalates, dialkyl or trialkyl trimellitates, dialkyl or trialkyl trimesates, dialkyl or trialkyl hemimellitates and dialkyl, trialkyl or tetraalkyl pyromellitates in which one or more of the alkyl groups contain 5, 6 or 7 carbon atoms (e.g., are C5, C6 or C7 alkyl groups) such alkyl groups include; n-pentyl, 1-methylbutyl terephthalate, 2-methylbutyl, 3-methylbutyl, 2,2-dimethylpropyl, 1,1-dimethylpropyl, n-hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-methyl-2-ethylpropyl, 1-ethyl-2-methylpropyl, 1-ethylbutyl, 2-ethylbutyl, n-heptyl, 1-methylhexyl, 2-methylhexyl, 3-methylhexyl, 4-methylhexyl, 5-methylhexyl, 1,1-dimethylpentyl, 2,2-dimethylpentyl, 3,3-dimethylpentyl, 4,4-dimethylpentyl, 1-ethylpentyl, 2-ethylpentyl, 3-ethylpentyl, 1,1,2-trimethylbutyl, 1,1,3-trimethylbutyl, 1,2,2-trimethylbutyl, 2,2,3-trimethylbutyl, 1,3,3-trimethylbutyl, 2,3,3-trimethylbutyl, 1,2,3-trimethylbutyl, 1-ethyl-2-methylbutyl, 1-ethyl-3-methylbutyl, 2-ethyl-3-methylbutyl and 1-methyl-2-ethylbutyl. Also envisaged as suitable are compounds in which the alkyl groups are not identical such as for example in butylpropyl terephthalate or where one of the alkyl groups is replaced by a benzyl group such as for example in butylbenzyl terephthalate. Also suitable are mixtures of one or more alkyl terephthalates, alkyl phthalates, alkyl isophthalates, dialkyl or trialkyl trimellitates, dialkyl or trialkyl trimesates, dialkyl or trialkyl hemimellitates and dialkyl, trialkyl or tetraalkyl pyromellitates in which one or more of the alkyl groups contain 5, 6 or 7 carbon atoms.

In the process of the present invention it is also possible to use mixtures of one or more of the benzenepolycarboxylic acid or a derivative thereof described herein. When the derivatives are esters the mixture may be derived through use of two or more alcohols in admixture or in sequence to esterify the same sample of a benzenepolycarboxylic acid derivative or a mixture of two or more benzenepolycarboxylic acids or derivatives. Alternatively the alcohols may be used to form, in separate syntheses, two different esterified derivatives, which may then be mixed together to form a mixture of two or more esterified derivatives. In either approach the mixture may comprise a mixture of esters derived from branched or linear alcohols, for example the mixture may comprise ester derivatives prepared from C7, C9, C8, C10 and C11 linear or branched alcohols, preferably linear alcohols, with the alcohols being used in the same synthesis of a mixture of derivatives or in separate syntheses of the derivative where the resultant derivative products in each synthesis are combined to form a mixed derivative. Preferably, the benzenepolycarboxylic acid or derivative thereof comprises a mixture of C7 dialkyl phthalates and C9 dialkyl phthalates, a mixture of C7 dialkyl terephthalates and C9 dialkyl terephthalates, a mixture of C7 dialkyl phthalates and C10 dialkyl phthalates, or a mixture of C7 dialkyl terephthalates and C10 dialkyl terephthalates.

In the process of the present invention, the preferred products are those derived from phthalates and in particular the following: cyclohexane-1,2-dicarboxylic acid di(isopentyl) ester, obtainable by hydrogenation of a di(isopentyl) phthalate having the Chemical Abstracts registry number (in the following: CAS No.) 84777-06-0; cyclohexane-1,2-dicarboxylic acid di(isoheptyl) ester, obtainable by hydrogenating the di(isoheptyl) phthalate having the CAS No. 71888-89-6; cyclohexane-1,2-dicarboxylic acid di(isononyl) ester, obtainable by hydrogenating the di(isononyl)phthalate having the CAS No. 68515-48-0; cyclohexane-1,2-dicarboxylic acid di(isononyl) ester, obtainable by hydrogenating the di(isononyl)phthalate having the CAS No. 28553-12-0, which is based on n-butene; cyclohexane-1,2-dicarboxylic acid di(isononyl) ester, obtainable by hydrogenating the di(isononyl)phthalate having the CAS No. 28553-12-0, which is based on isobutene; a 1,2-di-C9-ester of cyclohexanedicarboxylic acid, obtainable by hydrogenating the di(nonyl)phthalate having the CAS No. 68515-46-8; cyclohexane-1,2-dicarboxylic acid di(isodecyl) ester, obtainable by hydrogenating a di(isodecyl)phthalate having the CAS No. 68515-49-1; 1,2-C7-11-ester of cyclohexanedicarboxylic acid, obtainable by hydrogenating the corresponding phthalic acid ester having the CAS No. 68515-42-4; 1,2-di-C7-11-ester of cyclohexanedicarboxylic acid, obtainable by hydrogenating the di-C7-11-phthalates having the following CAS Nos.: 111381-89-6, 111381-90-9, 111381-91-0, 68515-44-6, 68515-45-7 and 3648-20-7; a 1,2-di-C9-11-ester of cyclohexanedicarboxylic acid, obtainable by hydrogenating a di-C9-11-phthalate having the CAS No. 98515-43-5; a 1,2-di(isodecyl)cyclohexanedicarboxylic acid ester, obtainable by hydrogenating a di(isodecyl)phthalate, consisting essentially of di-(2-propylheptyl)phthalate; 1,2-di-C7-9-cyclohexanedicarboxylic acid ester, obtainable by hydrogenating the corresponding phthalic acid ester, which comprises branched and linear C7-9-alkylester groups; respective phthalic acid esters which may be e.g. used as starting materials have the following CAS Nos.: di-C7-9-alkylphthalate having the CAS No. 111 381-89-6; di-C7-alkylphthalate having the CAS No. 68515-44-6; and di-C9-alkylphthalate having the CAS No. 68515-45-7.

More preferably, the above explicitly mentioned C5-7, C9, C10, C7-11, C9-11 and C7-9 esters of 1,2-cyclohexanedicarboxylic acids are preferably the hydrogenation products of the commercially available benzenepolycarboxylic acid esters with the trade names Jayflex® DINP (CAS No. 68515-48-0), Jayflex® DIDP (CAS No. 68515-49-1), Jayflex® DIUP (CAS No. 85507-79-5), Jayflex® DTDP (CAS No. 68515-47-9), Palatinol® 911P, Vestinol® 9 (CAS No. 28553-12-0), TOTM-I® (CAS No. 3319-31-1), Linplast® 68-TM and Palatinol® N (CAS No. 28553-12-0) which are used as plasticizers in plastics.

Further examples of commercially available benzenepolycarboxylic acid esters suitable for use in the present invention include phthalates such as: Palatinol® AH (Di-(2-ethylhexyl) phthalate; Palatinol® AH L (Di-(2-ethylhexyl) phthalate); Palatinol® C (Dibutyl phthalate); Palatinol® IC (Diisobutyl phthalate); Palatinol® N (Diisononyl phthalate); Palatinol® Z (Diisodecyl phthalate) Palatinol® 10-P (Di-(2-Propylheptyl) phthalate); Palatinol® 711P (Heptylundecyl phthalate); Palatinol® 911 (Nonylundecyl phthalate); Palatinol® 11P-E (Diundecyl phthalate); Palatinol® M (Dimethyl phthalate); Palatinol® A (Diethyl phthalate); Palatinol® A (Diethyl phthalate); and Palatinol® K (Dibutylglycol phthalate). Further examples are the commercially available adipates such as: Plastomoll® DOA (Di-(2-ethylhexyl) adipate) and Plastomoll® DNA (Diisononyl adipate). Further examples of suitable commercially available materials are Vestinol® C (DBP), Vestinol® IB (DIBP), Vestinol® AH (DEHP), Witamol® 110 (610P) and Witamol® 118 (810P).

In the process of the present invention, the hydrogenation is generally carried out at a temperature of from about 50 to 150° C., preferably from about 50 to 110° C., for example from about 60 to 100° C., in particular from about 70 to 90° C. The hydrogenation pressures used in the process of the present invention are generally above 10 bar, preferably from about 20 to about 200 bar, for example 50 to 120 bar, in particular 70 to 90 bar. Generally, the hydrogenation is carried out with a hydrogen excess of 30 to 250%, preferably 50 to 200%, for example 100 to 150%.

The process of the present invention may be carried out either continuously or batchwise, with preference being given to carrying out the process continuously. Preferably, when the process is carried out continuously, the process is carried out in a fixed bed reactor, for example a tubular reactor. Optionally, the process is carried out in a slurry reactor.

Preferably, when the process is carried out continuously, the liquid volume per volume of catalyst per hour (LVVH) is 1 to 5 hr$^{-1}$, preferably 2 to 5 hr'. LVVH is calculated, for example, by measuring the liquid flow rate in liters or m$^3$ per hour, and dividing the liquid flow rate by the catalyst volume in liters or m$^3$.

As hydrogenation gases, it is possible to use any gases which comprise free hydrogen and do not contain harmful amounts of catalyst poisons such as CO, $CO_2$, COS, $H_2S$ and amines. For example, waste gases from a reformer can be used. Preference is given to using pure hydrogen as the hydrogenation gas.

The hydrogenation of the present invention can be carried out in the presence or absence of a solvent or diluent, i.e. it is not necessary to carry out the hydrogenation in solution. However, preference is given to using a solvent or diluent. Any suitable solvent or diluent may be used. The choice is not critical as long as the solvent or diluent used is able to form a homogeneous solution with the benzenepolycarboxylic acid or derivate thereof to be hydrogenated. For example, the solvent or diluent may comprise water, in particular the solvent or diluent may comprise water in an amount of from 0.5 to 5 wt % based on the total weight of the feed stream. Preferably, the solvent or diluent is free of water.

Examples of suitable solvents or diluents include the following: straight-chain or cyclic ethers such as tetrahydrofuran or dioxane, and also aliphatic alcohols in which the alkyl radical preferably has from 1 to 10 carbon atoms, in particular from 3 to 6 carbon atoms. Examples of alcohols, which are preferably used, are i-propanol, n-butanol, i-butanol and n-hexanol. Preferably, the diluent comprises the hydrogenated product. Optionally, the diluent comprises light ends byproducts separated from the hydrogenated product. Preferably, the diluent comprises isoparaffinic fluids that can be easily separated from the hydrogenated product, such as isoparaffinic fluids available from ExxonMobil Chemical under the Isopar™ trade name. Examples of suitable isoparaffinic fluids include Isopar™ C, Isopar™ E, Isopar™ G, and Isopar™ H, preferably Isopar™ C and Isopar™ E. Mixtures of these or other solvents or diluents can likewise be used.

The amount of solvent or diluent used is not restricted in any particular way and can be selected freely depending on requirements. Typically, the amount of diluent used is selected to minimize the temperature rise across the catalyst bed in order to reduce byproduct formation, which is promoted by high catalyst temperatures. Preferably, the amount of diluent used is selected to provide a 10-70% strength based on the total weight of the solution of the benzenepolycarboxylic acid or derivate thereof to be hydrogenated. For example, the amount of solvent or diluent used is from 50 to 200% relative to the amount of benzenepolycarboxylic acid or derivative thereof used.

Preferably, the process comprises a two-stage hydrogenation step with an intermediate separation step. It may be that the two-stage hydrogenation step comprises: i) contacting a feed stream comprising the benzenepolycarboxylic acid or derivative thereof with a hydrogen-containing gas in the presence of a first catalyst in a first hydrogenation reactor under hydrogenation conditions to produce an at least partially hydrogenated intermediate product; ii) separating the at least partially hydrogenated intermediate product into a first intermediate fraction and a second intermediate fraction; iii) recycling the first intermediate fraction back to the first hydrogenation reactor, and iv) contacting the second intermediate faction with a hydrogen-containing gas in the presence of a second catalyst in a second hydrogenation reactor under hydrogenation conditions to produce the hydrogenated product. Optionally, the two-stage hydrogenation step additionally comprises: v) separating the hydrogenated product into a first product fraction and a second product fraction, and vi) recycling the first product fraction back to the second hydrogenation reactor. Preferably, the first intermediate fraction is a liquid phase fraction and the second intermediate fraction is a gas phase fraction.

Preferably the catalysts used in the first and second hydrogenation reactors both comprise ruthenium and rhodium. Preferably both these catalyst are the bimetallic ruthenium and rhodium catalyst described above. The catalysts used in the first and second hydrogenation reactors may be selected from the preferred bimetallic ruthenium and rhodium catalysts supported on silica described herein. These catalysts may have the same or different composition. Preferably the catalyst added to the first hydrogenation reactor is identical to the one added to the second reactor.

Preferably, when the process comprises a two-stage hydrogenation step, the first intermediate fraction is fed to the first hydrogenation reactor at a rate of from 50 to 200%, for examples 60 to 150%, such as 70 to 100%, of the rate that the feed stream comprising the benzenepolycarboxylic acid or derivative thereof is fed to the first hydrogenation reactor. Preferably, when the process comprises a two-stage hydrogenation step, and when the two stage hydrogenation step comprises separating the hydrogenated product into a first product fraction and a second product fraction and recycling the first product faction back to the second hydrogenation reactor, the first product fraction is fed to the second hydrogenation reactor at a rate of from 0 to 100%, for example 0 to 50%, such as 0 to 20%, of the rate that the second intermediate fraction is fed to the second hydrogenation reactor.

Optionally, when the process comprises a two-stage hydrogenation step, none of the hydrogenated product is recycled back to the second hydrogenation reactor.

It has been found that when the process comprises a two-stage hydrogenation step with an intermediate separation step, a fraction of the at least partially hydrogenated intermediate product provides a useful diluent for the first hydrogenation stage. It has also been found that when the process comprises a two-stage hydrogenation step, less diluent is required to control the temperature rise across the catalyst bed in the second stage than in the first stage.

In the process of the present invention it is also possible to use one or more derivatives of benzenepolycarboxylic acids in the unpurified state, that is, in the presence of one or more starting materials for their manufacture, for example alcohol in the case of ester derivatives. Traces of monoester derivatives, un-reacted acid such as phthalic acid, sodium monoester derivatives and sodium salts of the acids may also be present. Preferably, the benzenepolycarboxylic acid derivative is hydrogenated prior to purification, and after hydrogenation the product is sent to process finishing for stripping, drying and polishing filtration. For example, it may be that the benzenepolycarboxylic acid or derivative thereof is an intermediate feed containing high levels of alcohol in the case of ester derivatives. Excess alcohol in an amount of from 5 to 30% more than that required to achieve complete esterification of the acid may be present. For example, a feed comprising di-isononyl phthalate may comprise from 8 to 14 wt % isononyl alcohol, based on the weight of the feed.

In the process of the present invention the desired products are one or more cyclohexyl materials derived from the hydrogenation of the corresponding benzenepolycarboxylic acid or derivatives thereof. Ideally the benzenepolycarboxylic acid or derivatives thereof are converted to the desired product with a high degree of selectivity and with the maximum conversion possible of the benzenepolycarboxylic acid or derivatives thereof. Hydrogenations of this type often result in undesirable by-products of relatively low molecular weight and low boiling point; these by-products are referred to as "lights" or "light ends". In the context of the present invention "lights" are defined as materials in the as hydrogenated reaction product that are eluted before the object cyclohexyl materials when the as hydrogenated reaction product is analyzed by Gas Liquid Chromatography.

Details for one suitable method for determining the "lights" content of a product obtained by the process of the present invention is disclosed at page 9 of EP 2 338 870 A1. When using the process of the present invention it is possible to obtain greater than 95% conversion of the starting material (one or more benzenepolycarboxylic acid or derivatives thereof), whilst at the same time producing less than 1.5 wt % based on the total weight of reaction product of "lights". In the process of the present invention the product obtained directly from the hydrogenation reaction ideally contains the object cyclohexyl derivative(s) in an amount that equates to 97 or greater mole % conversion of the starting material, preferably 98.5 or greater mole % conversion, more preferably 99 or greater mole % conversion, and most preferably 99.9 or greater mole % conversion. In the process of the present invention the product obtained directly from the hydrogenation reaction ideally contains 1.3% or less, preferably 1.0% or less, more preferably 0.75% or less, even more preferably 0.5% or less, and in the most preferable embodiment less than 0.3 wt % based on the total weight of the reaction product of "lights". When hydrogenated products of this level of purity are obtained it may be possible to use these materials directly in certain applications without the need for further purification of the as hydrogenated product such as plasticisers for plastics products.

The catalyst used in the present invention comprises rhodium and ruthenium. It has to be noted in this respect that besides rhodium and ruthenium, the catalyst may additionally comprise other metals such as Group IB, VIIB, or VIIIB metals, for example platinum, iridium, palladium, rhenium, copper, silver and/or gold.

Optionally, the catalyst comprises rhodium in an amount of from about 0.05 to 2.5 wt %, preferably 0.1 to 1.5 wt %, for example 0.1 to 1 wt %, in particular 0.2 to 0.5 wt %, based on the total weight of the catalyst. Preferably, the catalyst comprises ruthenium in an amount of from about 0.05 to 2.5 wt %, preferably 0.1 to 1.5 wt %, for example 0.1 to 1 wt %, in particular 0.2 to 0.5 wt %, based on the total weight of the catalyst. Suitable methods for determining the metal content of the catalyst include, for example, mass balance during catalyst preparation, quantitative X-ray fluorescence analysis, and/or atomic adsorption. Preferably, the catalyst comprises rhodium and ruthenium in a ratio of from 0.1 to 10, in particular from 0.2 to 5, for example from 0.5 to 2. Optionally, the catalyst comprises rhodium and ruthenium in a 1:1 ratio. Catalysts comprising ruthenium and rhodium in a total amount of from about 0.05 to 5 wt %, preferably from 0.1 to 2.5 wt % and more preferably from 0.2 to 2 achieve good performances.

The catalyst used in the process of the invention comprises a support, for example a support comprising a porous inorganic material. Suitable support materials include silica, titanium dioxide, zirconium dioxide and alumina, for example alpha-alumina. Preferably, the support material comprises silica. Most preferably, the support material comprises silica in an amount of from 97 to 100 wt %, preferably 98 to 100 wt %, for example 99 to 100 wt %, such as 99.8-100 wt %, based on the total weight of the support. The support material may typically consist essentially of silica.

The catalyst used in the present invention may be prepared by any method known in the art. For example, the catalyst may be prepared by impregnation of the support material with a solution of a ruthenium metal salt and a rhodium metal salt. The metal salt solutions can be applied simultaneously or in succession. Optionally, the catalyst is prepared by impregnation of the support with a solution of a first metal salt followed by impregnation of the support with a solution of a second metal salt, wherein the first metal is ruthenium and the second metal is rhodium, or wherein the first metal is rhodium and the second metal is ruthenium. Preferably, the catalyst is prepared by impregnation of the support with a solution of a ruthenium salt and a rhodium salt. Generally speaking, when the ruthenium and/or the rhodium is applied by impregnation of the support, the concentration of the solution and the duration of the impregnation process is chosen in order to achieve the desired catalyst ruthenium and/or rhodium content. The ruthenium and/or rhodium may be applied to the support by steeping the support in aqueous ruthenium and/or rhodium salt solution, by spraying appropriate ruthenium and/or rhodium salt solutions onto the support, or by other suitable methods. Suitable ruthenium and/or rhodium metal salts for preparing the ruthenium and/or rhodium salt solutions are the nitrates, nitrosyl nitrates, halides, carbonates, carboxylates, acetylacetonates, chloro complexes, nitro complexes or amine complexes of ruthenium and/or rhodium, with preference being given to the nitrate and the nitrosyl nitrate complexes. Preferably, the ruthenium metal salt for preparing the ruthenium salt solution is ruthenium nitrate. Preferably, the rhodium metal salt for preparing the rhodium salt solution is rhodium nitrosyl nitrate.

Preferably, the catalyst is prepared by impregnation of the support material with a solution of a ruthenium metal salt and a rhodium metal salt, wherein the solution additionally comprises a dispersion aid. It may be that the dispersion aid is an organic ligand, for example an amino alcohol or amino acid ligand, preferably triethanolamine (TEA). Advantageously, the catalyst is prepared by impregnation of the support material with a solution of a ruthenium metal salt and a rhodium metal salt, wherein the solution additionally comprises TEA, and wherein the TEA is present in a molar ratio of at least 20 TEA to 1 metal, wherein "metal" is the combined ruthenium and rhodium content.

The impregnated catalyst is then preferably dried and optionally subjected to partial oxidation, for example calcination. The drying may be done at a temperature in the range of from 25 to 200° C., preferably 50 to 150° C. Calcination is preferably at a temperature in the range of from 250 to 500° C. Surprisingly, calcination of bimetallic ruthenium/rhodium catalysts supported on silica at a temperature between 350 and 450° C. provides catalysts with higher activity and/or selectivity.

The preferred catalysts are bimetallic ruthenium-rhodium catalyst s comprising from 0.05 to 1 wt % of ruthenium and, from 0.05 to 1 wt % of rhodium applied to a support comprising 99 to 100 wt % silica. More preferably these catalysts have been calcined at a temperature of between 350 and 450, typically between 375 and 425° C.

The support material with or without ruthenium and rhodium deposited thereon may be shaped into a wide variety of particle sizes. Optionally, the particles can be in the form of a powder, a granule, or a molded product, such as an extrudate. It may be that the support material is shaped into particles having an average diameter of from 0.5 to 5 mm. Preferably, the support material is extruded to form particles having a length of 2-15 mm and a diameter of 1-2 mm. A suitable method for determining the average diameter of particles is solid particle sieve analysis. Optionally, the shaped particles or extrudates have a size sufficient to pass through a 4 mesh (Tyler) screen and be retained on a 32 mesh (Tyler) screen. In cases where the catalyst is molded, such as by extrusion, the crystals can be extruded before drying or partially dried and then extruded. Preferably, the support is shaped into extrudates, spheres or tablets, either before or after application of the ruthenium and rhodium.

Preferably, in addition to the step of contacting a feedstream of benzenepolycarboxylic acid or derivative thereof with a hydrogen-containing gas in the presence of a catalyst under hydrogenation conditions to produce a hydrogenated product, the process additionally comprises at least one of the following steps: i) transferring the hydrogenated product to one or more reactors; ii) separating excess hydrogen from the hydrogenated product; iii) subjecting the hydrogenated product to steam stripping, preferably to remove light ends from the hydrogenated product; iv) drying the hydrogenated product by nitrogen stripping under vacuum; and, v) subjecting the hydrogenated product to a filtration step. For example, it may be that the process comprises at least two, at least three, at least four, or all five of steps i) to v). Preferably, when the feed stream comprises a diluent or solvent, and when the diluent or solvent comprises water, the process comprises the step of drying the hydrogenated product by nitrogen stripping under vacuum.

Generally speaking, when the feed stream comprises a diluent or solvent, at least a portion of the diluent or solvent is recycled to the step of contacting a feedstream of benzenepolycarboxylic acid or derivative thereof with a hydrogen-containing gas in the presence of a catalyst under hydrogenation conditions to produce a hydrogenated product. Optionally, when the process comprises the step of steam stripping the hydrogenated product to remove light ends, the light ends are used as a diluent and are recycled to the step of contacting a feedstream of benzenepolycarboxylic acid or derivative thereof with a hydrogen-containing gas in the presence of a catalyst under hydrogenation conditions to produce a hydrogenated product.

Optionally, the hydrogenated product is subjected to gas/liquid separation, for example after cooling to a temperature of from 20-50° C., to recover any excess hydrogen entrained in the product stream. It may be that separated excess hydrogen is recycled back to the hydrogenation reactor. Preferably, the hydrogenated product is filtered to remove any hydrogenation catalyst fines and then separated from byproducts formed during the hydrogenation process, for example using a continuous steam stripping column to remove light byproducts. Alternatively, it may be that a batch steam stripper is used. Optionally, the hydrogenated product is subjected to steam stripping at a temperature of 150-240° C. at reduced pressure, for example at a pressure of 50-900 mbara. Preferably, the steam to product ratio is in the range of in the range of 1-10%. It may be that the feed to the steam stripper is preheated using a feed/product heat exchanger, optionally followed by a steam preheating. Optionally, the steam stripped product is subjected to nitrogen stripping for removal of residual water. Preferably, the stripped, and optionally dried, product is filtered at a temperature of 70-120° C. Alternatively, the stripped, and optionally dried, product is subjected to treatment with an adsorbent as described in EP 1 663 940 and then filtered, optionally with the use of a filter aid. Any kind of filter can be used, such as cartridge, candle or plate filters, depending upon the quantity of solids to be removed.

Preferably, the hydrogenated product is subjected to a filtration step, wherein the hydrogenated product is filtered by contacting the hydrogenated product with a precoated filter or a cartridge filter.

The process of the present invention is further illustrated by means of the following non-limiting examples.

EXAMPLES

Comparative Examples 1, 2 and 3

Comparative catalyst samples C1, C2 and C3 were prepared by the incipient wetness procedure. 1.462 g of triethanolamine (TEA) was added to 3.33 g of an aqueous solution of ruthenium nitrosyl nitrate having a ruthenium concentration of 1.5 wt %, based on the weight of the solution. Deionized water was added to bring the total solution volume to 12.0 ml. 9.90 g of Davisil™ 646 silica was impregnated with the solution by incipient wetness and then dried at 100° C. overnight. The resulting dried catalyst was designated C1. The ruthenium content of C1 was 0.5 wt %, based on the total weight of the catalyst.

1 g of C1 was calcined at 0.5° C./min to 250° C. and then held at that temperature for an hour. The resulting calcined catalyst was designated C2. The ruthenium content of C2 was 0.5 wt %, based on the total weight of the catalyst.

Another 1 g of C1 was calcined at 0.5° C./min to 400° C. and then held at that temperature for 10 hours. The resulting calcined catalyst was designated C3. The ruthenium content of C3 was 0.5 wt %, based on the total weight of the catalyst.

Comparative Example 4

Comparative catalyst sample C4 was prepared by the incipient wetness procedure. The preparation of C4 was the same as that for C2, except that the final calcination temperature was 275° C., at which temperature the sample was held for four hours. The ruthenium content of C4 was 0.5 wt %, based on the total weight of the catalyst.

Comparative Examples 5, 6 and 7

Comparative catalyst samples C5, C6 and C7 were prepared by incipient wetness procedure. 1.462 g of TEA was added to 0.495 g of an aqueous solution of rhodium nitrate having a rhodium concentration of 10.10 wt %, based on the weight of the solution. A few added drops of nitric acid aided the dissolution of the components. Deionized water was added to bring the total solution volume to 12.0 ml. 9.90 g of Davisil™ 646 silica was impregnated with the solution by incipient wetness and then dried at 100° C. overnight. The resulting dried catalyst was designated C5. The rhodium content of C5 was 0.5 wt %, based on the total weight of the catalyst.

1 g of C5 was calcined at 0.5° C./min to 250° C. and then held at that temperature for an hour. The resulting calcined catalyst was designated C6. The rhodium content of C6 was 0.5 wt %, based on the total weight of the catalyst.

Another 1 g of C5 was calcined at 0.5° C./min to 400° C. and then held at that temperature for 10 hours. The resulting calcined catalyst was designated C7. The rhodium content of C7 was 0.5 wt %, based on the total weight of the catalyst.

Comparative Example 8

Comparative catalyst sample C8 was prepared by the incipient wetness procedure. The preparation of C8 was the same as that for C7, except that the support material used was Davisil™ 62 and the volume of the impregnation solution was adjusted to ensure that it was sufficient to reach the appropriate incipient wetness volume. C8 was calcined at 0.5° C./min to 400° C. and then held at that temperature for 4 hours. The rhodium content of C8 was 0.5 wt %, based on the total weight of the catalyst.

Comparative Example 9

Comparative catalyst sample C9 was prepared by the incipient wetness procedure. The preparation of C9 was the same as that for C8, except that the amount of rhodium precursor and TEA was adjusted so that the rhodium content of C9 was 1 wt %, based on the total weight of the catalyst. C9 was calcined at 0.5° C./min to 400° C. and then held at that temperature for 4 hours.

Comparative Examples 10 and 11

Comparative catalyst samples C10 and C11 were prepared by the incipient wetness procedure without the use of TEA. 5.00 g of an aqueous solution of ruthenium nitrosyl nitrate having a ruthenium concentration of 1.5 wt %, based on the total weight of the solution, was diluted with sufficient water to reach the appropriate incipient wetness volume and then used to impregnate 15 g of Davisil™ 663 silica. After impregnation, the sample was dried at 100° C. for 4 hours. The resulting dried catalyst was designated C10. The ruthenium content of C10 was 0.5 wt %, based on the total weight of the catalyst.

A portion of C10 was calcined at 1° C./min to 300° C. and then held at that temperature for one hour. The resulting calcined catalyst was designed C11. The ruthenium content of C11 was 0.5 wt %, based on the total weight of the catalyst.

Comparative Example 12

Comparative catalyst sample C12 was prepared by the incipient wetness procedure. 3.71 g of TEA was added to 8.37 g of an aqueous solution of ruthenium nitrosyl nitrate having a ruthenium concentration of 1.5 wt %, based on the total weight of the solution, and sufficient water was added to reach the incipient wetness volume. 25 g of Davisil™ 663 silica was treated with the solution. The impregnate was then dried at 100° C. for 4 hours. A portion of the dried impregnate was calcined at 1° C./min to 400° C. and then held at that temperature for 3 hours. The resulting calcined catalyst was designated C12. The ruthenium content of C12 was 0.5 wt %, based on the total weight of the catalyst.

Comparative Example 13

Comparative catalyst sample C13 was prepared by the incipient wetness procedure. 3.73 g of TEA was added to 8.37 g of an aqueous solution of ruthenium nitrosyl nitrate having a ruthenium concentration of 1.5 wt %, based on the total weight of the solution, and sufficient water added to reach the incipient wetness volume. The solution was stirred until it was clear. The molar ratio of Ru to TEA was 21. SIPERNAT® 50 silica was treated with the solution. The impregnate was dried in air at 100° C. for 12 hours and then calcined in air at 275° C. for 1 hour with ramping rate of 5° C./min. The air flow rate inside the calciner was adjusted at 5 volume/volume catalyst/minute. The resulting calcined catalyst was designated C13. The ruthenium content of C13 was 0.5 wt %, based on the total weight of the catalyst.

Comparative Example 14

Comparative catalyst sample C14 was prepared by the incipient wetness procedure. 3.73 g of TEA was added to 8.37 g of an aqueous solution of ruthenium nitrosyl nitrate having a ruthenium concentration of 1.5 wt %, based on the total weight of the solution, and sufficient water added to reach the incipient wetness volume. The solution was stirred until it was clear. The molar ratio of Ru to TEA was 21. Aerolyst® 3041 silica was treated with the solution. The impregnate was dried in air at 100° C. for 12 hours and then calcined in air at 275° C. for 1 hour with ramping rate of 5° C./min. The air flow rate inside the calciner was adjusted at 5 volume/volume catalyst/minute. The resulting calcined catalyst was designated C14. The ruthenium content of C14 was 2.5 wt %, based on the total weight of the catalyst.

Example 1

Example catalyst sample E1 was prepared by the incipient wetness procedure without the use of TEA. 3.33 g of an aqueous solution of ruthenium nitrosyl nitrate having a ruthenium concentration of 1.5 wt %, based on the total weight of the ruthenium solution, was combined with 0.495 g of an aqueous solution of rhodium nitrate having a rhodium concentration of 10.10 wt %, based on the total weight of the rhodium solution. The combined solutions were dissolved in deionized water so that the total solution volume was 12.0 ml. 9.90 g of Davisil™ 646 silica was impregnated with the solution by incipient wetness and then dried at 100° C. overnight. The resulting dried catalyst was designated E1. The ruthenium content of E1 was 0.5 wt %, and the rhodium content of E1 was 0.5 wt %, based on the total weight of the catalyst.

Examples 2, 3 and 4

Example catalyst samples E2, E3 and E4 were prepared by incipient wetness procedure. 3.33 g of an aqueous solution of ruthenium nitrosyl nitrate having a ruthenium concentration of 1.5 wt %, based on the total weight of the ruthenium solution, was combined with 0.495 g of an aqueous solution of rhodium nitrate having a rhodium concentration of 10.10 wt %, based on the total weight of the rhodium solution, and with 2.923 g of TEA. A few added drops of nitric acid aided the dissolution of the components. Deionized water was added to bring the total solution volume to 12.0 ml. 9.90 g of Davisil™ 646 silica was impregnated with the solution by incipient wetness and then dried at 100° C. overnight. The resulting dried catalyst was designated E2. The ruthenium content of E2 was 0.5 wt % and the rhodium content of E4 was 0.5 wt %, based on the total weight of the catalyst.

1 g E2 was calcined at 0.5° C./min to 250° C. and then held at that temperature for an hour. The resulting calcined catalyst was designated E3. The ruthenium content of E4 was 0.5 wt % and the rhodium content of E3 was 0.5 wt %, based on the total weight of the catalyst.

Another 1 g of E2 was calcined at 0.5° C./min to 400° C. and then held at that temperature for 10 hours. The resulting calcined catalyst was designated E4. The ruthenium content of E4 was 0.5 wt % and the rhodium content of E4 was 0.5 wt %, based on the total weight of the catalyst.

Example 5

Example catalyst sample E5 was prepared by the incipient wetness procedure. 2.67 g of an aqueous solution of ruthenium nitrosyl nitrate having a ruthenium concentration of 1.5 wt %, based on the total weight of the ruthenium solution, was combined with 0.396 g of an aqueous solution of rhodium nitrate having a rhodium concentration of 10.10 wt %, based on the total weight of the rhodium solution, and with 2.34 g of TEA. A few added drops of nitric acid aided the dissolution of the components. Deionized water was added to bring the total solution volume to 17.8 ml. 19.8 g of 1 mm silica spheres available from Johnson Matthey (precalcined at 500° C.) was impregnated with the solution by incipient wetness and then dried at 100° C. overnight. The resulting dried catalyst sample was calcined at 0.5° C./min to 400° C. and then held at that temperature for 10 hours. The resulting calcined catalyst sample was designated E5. The ruthenium content of E5 was 0.2 wt % and the rhodium content of E5 was 0.2 wt %, based on the total weight of the catalyst.

Example 6

Example catalyst sample E6 was prepared by the incipient wetness procedure. 1.33 g of an aqueous solution of ruthenium nitrosyl nitrate having a ruthenium concentration of 1.5 wt %, based on the total weight of the ruthenium solution, was combined with 0.198 g of an aqueous solution of rhodium nitrate having a rhodium concentration of 10.10 wt %, based on the total weight of the rhodium solution, and with 1.17 g of TEA. A few added drops of nitric acid aided the dissolution of the components. Deionized water was added to bring the total solution volume to 17.8 ml. 19.8 g of 1 mm silica spheres (precalcined at 500° C.) was impregnated with the solution by incipient wetness and then dried at 100° C. overnight. The resulting dried catalyst sample was calcined at 0.5° C./min to 400° C. and then held at that temperature for 10 hours. The resulting calcined catalyst sample was designated E6. The ruthenium content of E6 was 0.1 wt % and the rhodium content of E6 was 0.1 wt %, based on the total weight of the catalyst.

Example 7

Example catalyst sample E7 was prepared by the incipient wetness procedure. 0.495 g of an aqueous solution of rhodium nitrate having a rhodium concentration of 10.10 wt %, based on the total weight of the rhodium solution, was combined with 1.45 g of TEA. Deionized water was added to bring the total solution volume to 11 ml. 9.95 g of Davisil™ 646 silica was impregnated with the solution by incipient wetness, and then dried at 100° C. and calcined at 400° C. 3.33 g of an aqueous solution of ruthenium nitrosyl nitrate having a ruthenium concentration of 1.5 wt %, based on the total weight of the ruthenium solution, was combined with 1.46 g of TEA and 8.8 g of deionized water. The calcined rhodium/silica sample was impregnated with this ruthenium solution. The resulting catalyst sample was dried at 100° C. overnight and then calcined at 250° C. for 1 hour. The resulting calcined catalyst sample was designated E7. The rhodium content of E1 was 0.5 wt %, and the ruthenium content of E7 was 0.5 wt %, based on the total weight of the catalyst.

The comparative catalyst samples and the example catalyst samples are summarized in Table 1.

TABLE 1

| Catalyst Sample | Comparative/ Inventive | Dispersion Aid | Support Material | Ru Content (wt %) | Rh Content (wt %) | Final Calcination Temperature (° C.) |
|---|---|---|---|---|---|---|
| C1 | Comparative | TEA | Davisil™ 646 silica | 0.5 | 0 | Not calcined |
| C2 | Comparative | TEA | Davisil™ 646 silica | 0.5 | 0 | 250 |
| C3 | Comparative | TEA | Davisil™ 646 silica | 0.5 | 0 | 400 |
| C4 | Comparative | TEA | Davisil™ 646 silica | 0.5 | 0 | 275 |

TABLE 1-continued

| Catalyst Sample | Comparative/ Inventive | Dispersion Aid | Support Material | Ru Content (wt %) | Rh Content (wt %) | Final Calcination Temperature (° C.) |
|---|---|---|---|---|---|---|
| C5 | Comparative | TEA | Davisil ™ 646 silica | 0 | 0.5 | Not calcined |
| C6 | Comparative | TEA | Davisil ™ 646 silica | 0 | 0.5 | 250 |
| C7 | Comparative | TEA | Davisil ™ 646 silica | 0 | 0.5 | 400 |
| C8 | Comparative | TEA | Davisil ™ 62 silica | 0 | 0.5 | 400 |
| C9 | Comparative | TEA | Davisil ™ 62 silica | 0 | 1 | 400 |
| C10 | Comparative | None | Davisil ™ 663 silica | 0.5 | 0 | Not calcined |
| C11 | Comparative | None | Davisil ™ 663 silica | 0.5 | 0 | 300 |
| C12 | Comparative | TEA | Davisil ™ 663 silica | 0.5 | 0 | 400 |
| C13 | Comparative | TEA | SIPERNAT ® 50 silica | 0.5 | 0 | 275 |
| C14 | Comparative | TEA | Aerolyst ® 3041 silica | 2.5 | 0 | 275 |
| E1 | Inventive | None | Davisil ™ 646 silica | 0.5 | 0.5 | Not calcined |
| E2 | Inventive | TEA | Davisil ™ 646 silica | 0.5 | 0.5 | Not calcined |
| E3 | Inventive | TEA | Davisil ™ 646 silica | 0.5 | 0.5 | 250 |
| E4 | Inventive | TEA | Davisil ™ 646 silica | 0.5 | 0.5 | 400 |
| E5 | Inventive | TEA | 1 mm Silica spheres | 0.2 | 0.2 | 400 |
| E6 | Inventive | TEA | 1 mm Silica spheres | 0.1 | 0.1 | 400 |
| E7 | Inventive | TEA | Davisil ™ 646 silica | 0.5 | 0.5 | 400 (Rh only) 250 (Rh + Ru) |

Catalyst Characterization

Chemisorption measurements were obtained under static high vacuum conditions on a Quantachrome Autosorb 1A instrument. Approximately 0.4 g of catalyst was reduced in flowing hydrogen and heated at 2° C./min to the final reduction temperature and held at that temperature for 2 hours. For a reduction temperature of 400° C., experiments were also carried out in which the sample was held at 400° C. for an extra 2 hours and an extra 4 hours, i.e. the samples were held at 400° C. for 4 hours and 6 hours in total, respectively. Following reduction, the sample was evacuated (while still at the reduction temperature) with a turbomolecular pump for 30 minutes to remove any chemisorbed hydrogen. With the sample still under vacuum, the temperature was lowered to 40° C. and held isothermal during subsequent treatments. An 8-point isotherm (with pressures between 80 and 650 torr, 10.7 and 86.7 kPa) was measured at 40° C. with $H_2$ as the absorbate molecule. Extrapolation of the linear portion of this curve to zero pressure gives the total or combined absorption uptake. The sample was then evacuated (at 40° C.) to remove the weakly chemisorbed hydrogen, and the weak (or backsorption) isotherm measured. Subtraction of the two isotherms yields the strong (or difference) isotherm.

We have found that crystallite sizes extrapolated from the combined isotherm for ruthenium and ruthenium-rhodium alloys and the strong isotherm for rhodium, all with a stoichiometry of 1 H per metal, correlate with TEM measured sizes. The chemisorption uptake for each bimetallic ruthenium-rhodium catalyst is expressed in terms of the equivalent wt % of rhodium for a corresponding monometallic rhodium catalyst, i.e. the combined rhodium and ruthenium content, in moles, is normalized to an equivalent rhodium wt %.

Thermogravimetric Analysis/Differential Thermal Analysis/Mass Spectrometry (TGA/DTA/MS) measurements—approximately 110 mg of catalyst were loaded into a Mettler TGA 851 thermal balance. The catalysts were treated under flowing air (50 cc/min, 50 ml/min) at one atmosphere total pressure. The samples were measured by an integrated thermopile to address the relative strength of the endothermic and exothermic events.

The Thermogravimetric/Differential Scanning calorimetry (TG/DSC) pattern for catalyst sample E2 in FIG. 1 shows that the bimetallic TEA impregnate decomposes in a multistep pattern similar to that of a monometallic catalyst. The precursor metal complex starts to decompose at temperatures above 150° C., with a large exotherm at about 385° C. The exotherm at around 385° C. demonstrates a single sharp decomposition, and not two separate events as we would expect in if the catalyst sample comprised a physical mixture of the two, individual, precursor metal complex impregnates.

Figure 2:
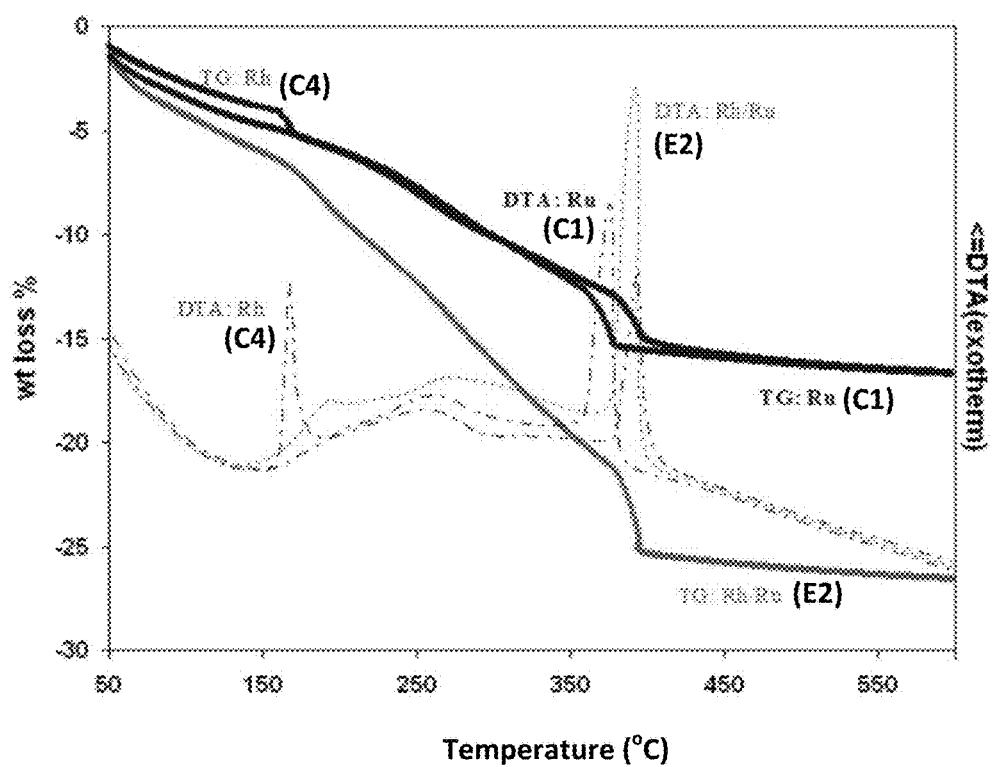
FIG. 2 shows TG/DTA graph for comparative example catalyst samples C1 and C4 and example catalyst sample E2.

The TG/DSC patterns for comparative catalyst samples C1 and C5 are illustrated in FIG. 2, together with the TG/DSC pattern for catalyst sample E2. FIG. 2 shows the two separate exotherms of the ruthenium (C1) and rhodium (C5) monometallic catalyst systems, which would be expected for catalyst sample E2 if catalyst sample E2 comprised a physical mixture of ruthenium and rhodium, rather than a bimetallic alloy.

Figure 3:
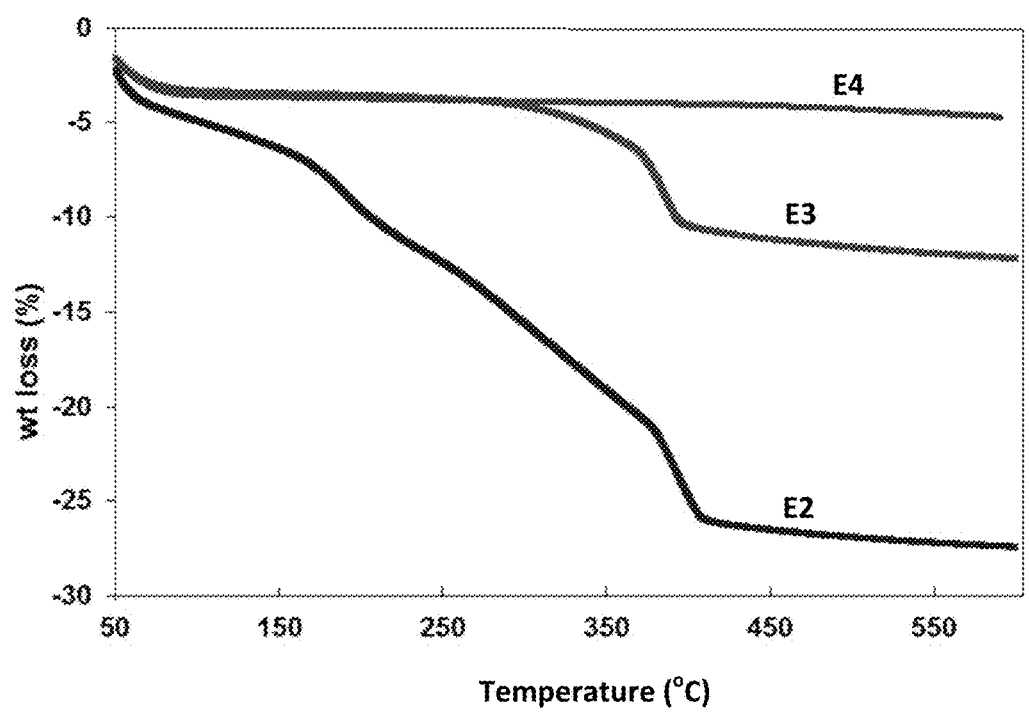
FIG. 3 shows a TG graph for example catalyst samples E2, E3 and E4.

It is also possible to estimate from FIG. 2 the calcination temperature required to fully remove the organic fragment of the metal complex precursor after impregnation of the support, and the calcination temperature required to prepare the remnant form of the catalyst, that is, the form in which the deposited metal complex is oxidized but a remnant of the organic fragment remains. The TG traces for comparative catalyst samples C1 and C5, and for catalyst sample E2, show that the organic component of the metal complex precursor is completely lost above 400° C., whereas the remnant form is generated at around 250° C. FIG. 3 confirms that the remnant form of the rhodium/ruthenium complex remains after calcination at 250° C., while the complex is totally decomposed after calcination at 400° C.

Figure 4:
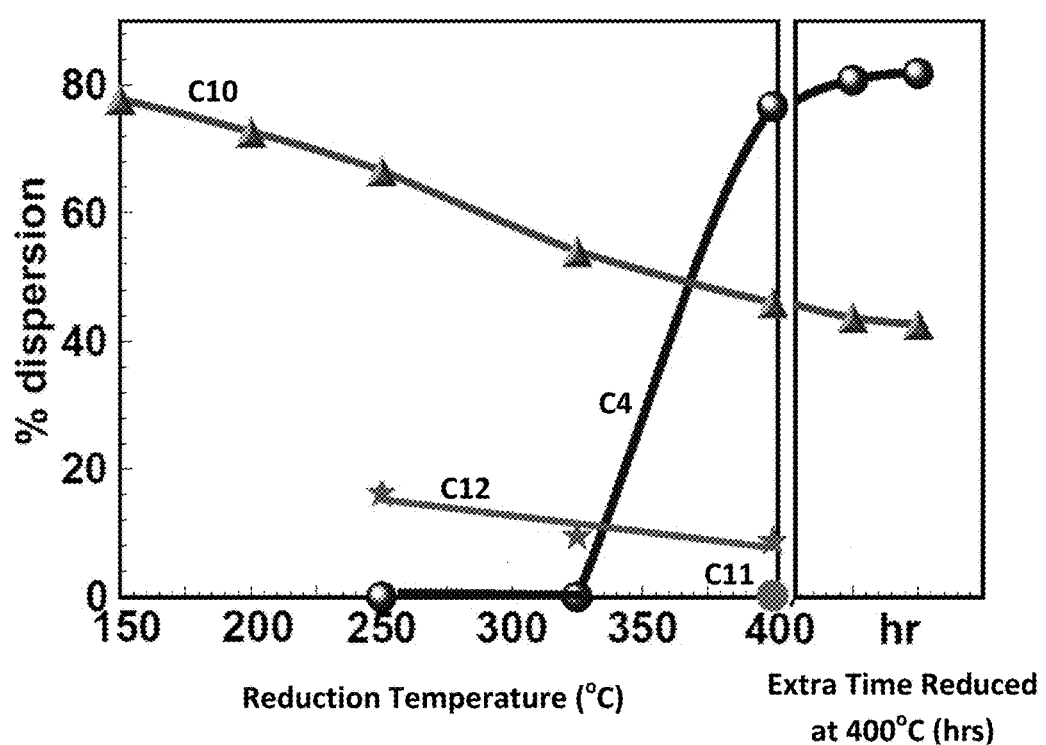
FIG. 4 shows a H2 chemisorption graph for comparative example catalyst samples C4, C10, C11 and C12.

The chemisorption data of monometallic ruthenium catalyst samples C4, C10, C11 and C12 following reduction at temperatures ranging from 150 to 400° C. are listed in Table 2 and plotted in FIG. 4.

TABLE 2

| Catalyst Sample | Reduction Temp. (° C.) | H/Ru (combined) | H/Ru (weak) | H/Ru (strong) |
|---|---|---|---|---|
| C4 | 250 | 0 | 0 | 0.0 |
| Ru content: 0.5 wt % | 325 | 0 | 0 | 0.0 |
| Calcined at 275° C. | 400 | 79.9 | 36.56 | 43.3 |
|  | 400 (+2 hrs) | 82.3 | 37.45 | 44.8 |
|  | 400 (+4 hrs) | 83.6 | 38.81 | 44.8 |
| C10 | 150 | 77.8 | 40.9 | 36.9 |
| Ru content: 0.5 wt % | 200 | 72.7 | 38.2 | 34.4 |
| Prepared without TEA | 250 | 66.5 | 36.5 | 30 |
| Dried at 100° C. | 325 | 54 | 32.6 | 21.4 |
|  | 400 | 46 | 27.7 | 18.3 |
|  | 400 (+2 hrs) | 43.7 | 27.2 | 16.5 |
|  | 400 (+4 hrs) | 42.6 | 25.8 | 16.8 |
| C11 | 250 | 1.22 | 0 | 1.2 |
| Ru content: 0.5 wt % | 325 | 0.38 | 0 | 0.4 |
| Prepared without TEA | 400 | 0.23 | 0 | 0.2 |
| Calcined at 300° C. |  |  |  |  |
| C12 | 250 | 16.2 | 7.0 | 9.2 |
| Ru content: 0.5 wt % | 325 | 9.5 | 4.0 | 5.5 |
| Calcined at 400° C. | 400 | 8.7 | 1.7 | 7.0 |
|  | 400 (+2 hrs) | 6.7 | 0 | 6.7 |

The chemisorption data of monometallic rhodium catalyst samples C8 and C9 following reduction at temperatures ranging from 150 to 400° C. are listed in Table 3.

TABLE 3

| Catalyst Sample | Reduction Temp. (° C.) | H/Rh (combined) | H/Rh (weak) | H/Rh (strong) |
|---|---|---|---|---|
| C8 | 150 | 101.6 | 48.1 | 53.5 |
| Rh content: 0.5 wt % | 250 | 122.8 | 46.3 | 76.5 |
| Calcined at 400° C. | 325 | 121.8 | 51.1 | 70.7 |
|  | 400 | 118.9 | 54.4 | 64.5 |
|  | 400 (+2 hrs) | 116.4 | 54.0 | 62.4 |
|  | 400 (+4 hrs) | 116.6 | 51.2 | 65.4 |
| C9 | 250 | 78.4 | 38.8 | 39.6 |
| Rh content: 1 wt % | 325 | 71.1 | 35.8 | 35.3 |
| Calcined at 400° C. | 400 | 67.2 | 33.8 | 33.4 |
|  | 400 (+2 hrs) | 69.1 | 35.0 | 34.0 |

The preferred pretreatment for monomeric ruthenium catalyst samples is low temperature calcination (275° C. for C4), and the preferred chemisorption protocol is the "H/Ru (combined)" uptake. The preferred pretreatment for the monomeric rhodium catalyst samples is high temperature calcination (400° C. for C8), and the preferred chemisorption profile is the "H/Rh (strong) uptake". Both monomeric comparative catalyst samples C4 and C8 show 70-80% dispersion using the preferred pretreatment and chemisorption protocol for the metal.

Figure 5:
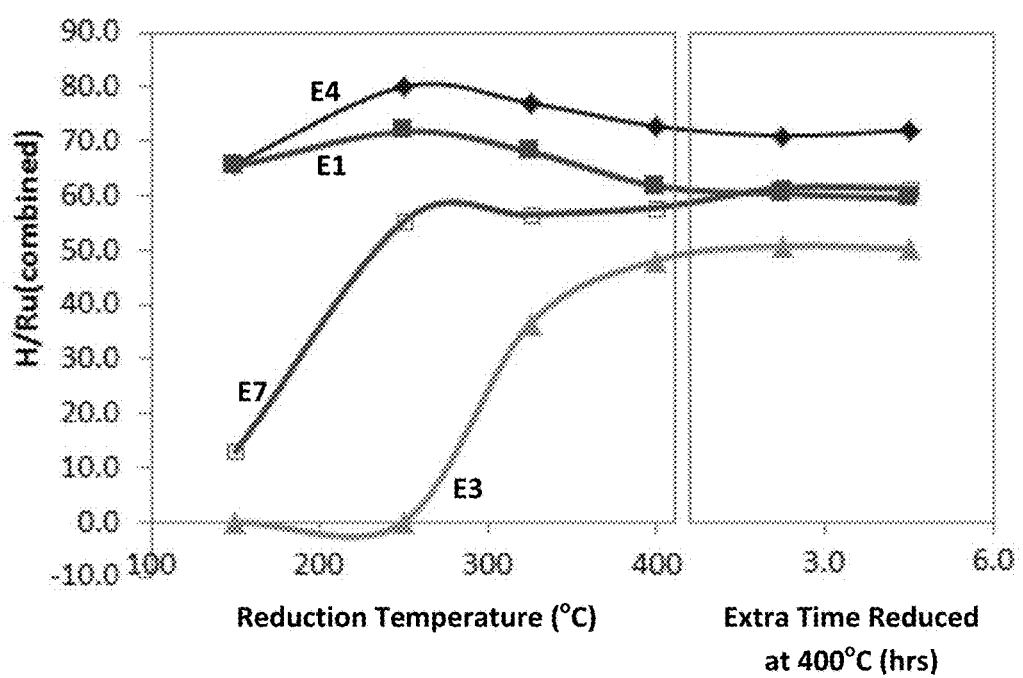
FIG. 5 shows a H2 chemisorption graph for example catalyst samples E1, E3, E4 and E7.

The chemisorption data of catalyst samples E1, E3, E4 and E7 following reduction at temperatures ranging from 150 to 450° C. are listed in Table 4 and plotted in FIG. 5.

TABLE 4

| Catalyst Sample | Reduction Temp. (° C.) | H/Ru (combined) | H/Ru (weak) | H/Ru (strong) |
|---|---|---|---|---|
| E1 | 150 | 65.4 | 28.7 | 36.7 |
| Ru content: 0.5 wt % | 250 | 71.8 | 31.4 | 40.4 |
| Rh content: 0.5 wt % | 325 | 68 | 29.8 | 38.2 |
| Measured as: | 400 | 61.7 | 28.4 | 33.3 |
| 0.99 wt % Ru | 400 (+2 hrs) | 60.3 | 28.7 | 31.6 |
| Prepared without TEA | 400 (+4 hrs) | 59.5 | 26.5 | 33 |
| Dried at 100° C. | 450 | 59.1 | 28 | 31.1 |
| E3 | 150 | 0 | 0 | 0 |
| Ru content: 0.5 wt % | 250 | 0 | 0 | 0 |
| Rh content: 0.5 wt % | 325 | 36.5 | 14.2 | 22.3 |
| Measured as: | 400 | 48.1 | 24.2 | 23.9 |
| 0.99 wt % Ru | 400 (+2 hrs) | 50.7 | 30.7 | 20 |
| Dried at 100° C. | 400 (+4 hrs) | 50.2 | 25.1 | 25.1 |
| Calcined at 250° C. |  |  |  |  |
| E4 | 150 | 65.9 | 28.4 | 37.5 |
| Ru content: 0.5 wt % | 250 | 80.1 | 32.1 | 48 |
| Rh content: 0.5 wt % | 325 | 77.1 | 32.6 | 44.5 |
| Measured as: | 400 | 72.8 | 33.3 | 39.5 |
| 0.99 wt % Ru | 400 (+2 hrs) | 71 | 32.3 | 38.7 |
| Dried at 100° C. | 400 (+4 hrs) | 72.1 | 34.5 | 37.6 |
| Calcined at 400° C. | 450 | 69.8 | 28.2 | 41.6 |
| E5 | 250 | not measured | not measured | 47.7 |
| Ru content: 0.2 wt % |  |  |  |  |
| Rh content: 0.2 wt % |  |  |  |  |
| Dried at 100° C. |  |  |  |  |
| Calcined at 400° C. |  |  |  |  |
| E6 | 250 | not measured | not measured | 42.0 |
| Ru content: 0.1 wt % |  |  |  |  |
| Rh content: 0.1 wt % |  |  |  |  |
| Dried at 100° C. |  |  |  |  |
| Calcined at 400° C. |  |  |  |  |
| E7 | 150 | 12.9 | 9.3 | 3.6 |
| Ru content: 0.5 wt % | 250 | 55.3 | 24.3 | 31 |
| Rh content: 0.5 wt % | 325 | 56.5 | 26.9 | 29.6 |
| Measured as: | 400 | 57.8 | 28 | 29.8 |
| 0.99 wt % Ru | 400 (+2 hrs) | 61.4 | 28.4 | 33 |
| Dried at 100° C. | 400 (+4 hrs) | 61.3 | 25.4 | 35.9 |
| Calcined at 400° C. & 250° C. | 450 | 60.5 | 28.3 | 32.2 |

Surprisingly, the chemisorption data for the bimetallic ruthenium-rhodium catalyst sample listed in Table 4 show that 70-80% dispersion (H/Ru uptake) is achieved with a calcination temperature of 400° C. That result contrasts with the chemisorption of ruthenium monometallic comparative catalyst sample C12 (calcined at 400° C.) which had a dispersion of around 10% (see Table 2 and FIG. 4). The unexpected finding that the metal centers of a bimetallic ruthenium-rhodium catalyst calcined at 400° C. are well dispersed was confirmed by the TEM data.

Figure 6:
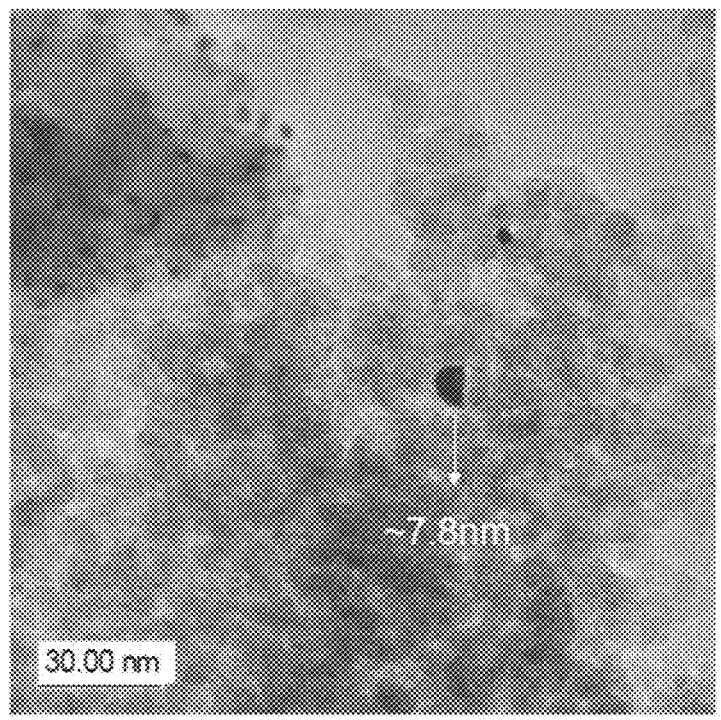
FIG. 6 shows TEM images of example catalyst sample E1 following reduction at 450° C.
Figure 6:
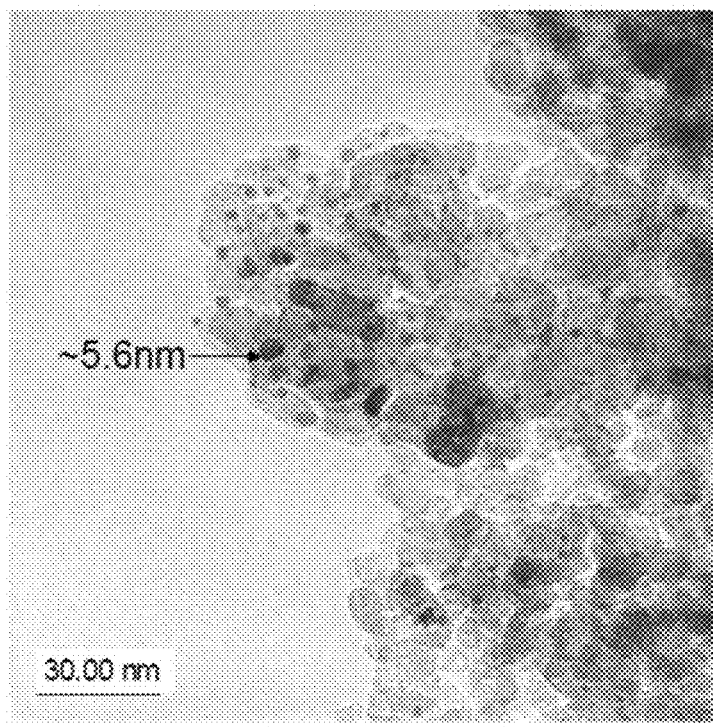
Figure 7:
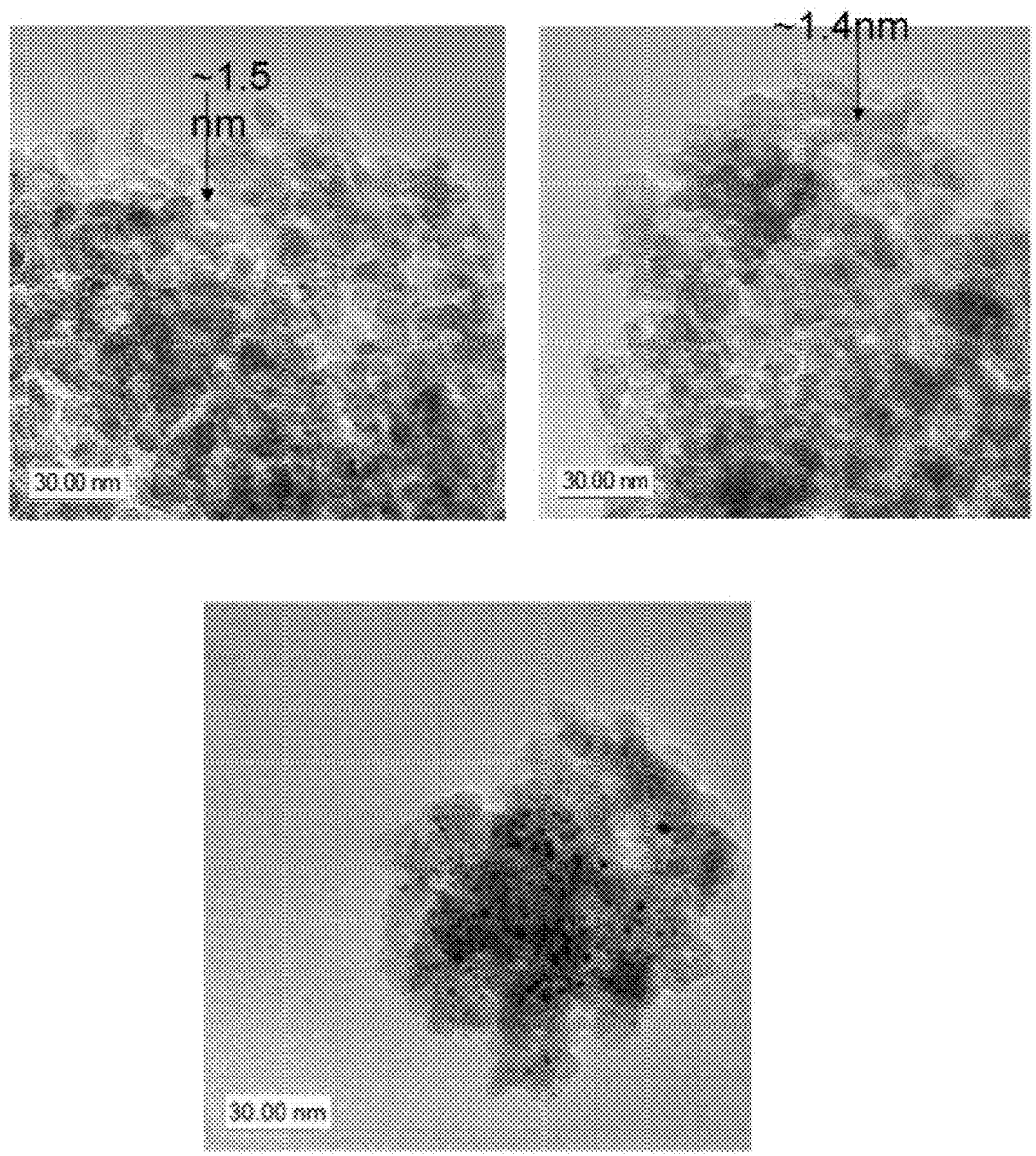
FIG. 7 shows TEM images of example catalyst sample E3 following reduction at 400° C.
Figure 8:
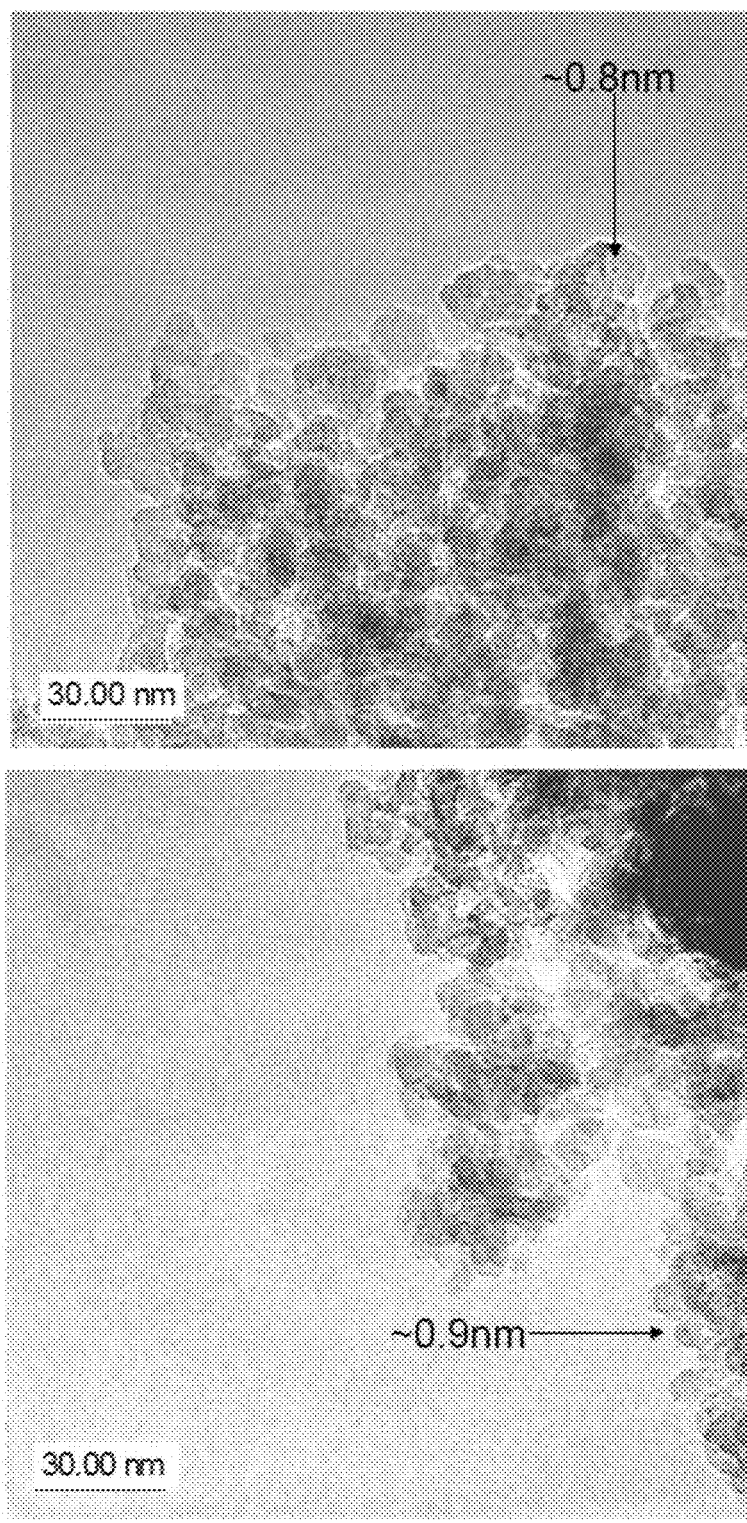
FIG. 8 shows TEM images of example catalyst sample E4 following reduction at 400° C.

TEM data were collected on example catalyst samples E1, E3 and E4 (samples comprising 0.5 wt % ruthenium and 0.5 wt % rhodium on silica prepared in the absence of TEA and with TEA, separate samples of the latter calcined at 250° C. and 400° C., respectively). The results are shown in FIGS. 6, 7 and 8. The TEM of FIG. 6 shows inhomogeneously distributed, large metal particles. The TEM of FIG. 7 shows mainly homogeneous particle distribution but with at least one region of more closely packed metal particles. The TEM of FIG. 8 shows homogeneous metal particle distribution. The sample with the smallest particles and with the most homogeneous distribution is the TEA impregnate calcined at 400° C. (FIG. 8). It contains particles of about 1 nm in size, a size which correlates with the high chemisorption values seen in the combined measurement.

Typically, supported monometallic ruthenium catalysts are prepared by subjecting the dried, impregnated support to partial oxidation (for example, calcination at temperatures of 250-300° C.), followed by high temperature reduction (for example, reduction at a temperature of about 400° C.). At higher calcination temperatures (for example, 400° C.), ruthenium oxides often migrate and grow into large particles. The low chemisorption of comparative catalyst sample C12 (see Table 2 and FIG. 4) is believed to result from such migration and agglomeration of ruthenium when supported monometallic ruthenium catalysts are calcined at 400° C. The high chemisorption of the supported bimetallic ruthenium-rhodium catalysts of the present invention following calcination at higher temperatures (for example, 400° C. or 450° C.) was therefore unexpected.

It is believed that the alloy formed by ruthenium and rhodium in the catalyst of the present invention does not migrate and agglomerate during calcination at temperatures of about 400 to 450° C.

Example 8

Catalysis

The silica-supported ruthenium monometallic catalysts of Comparative Examples 13 (catalyst sample C13 having a ruthenium content of 0.5% based on the total weight of the catalyst, supported on silica, calcined at 275° C.) and 14 (catalyst sample C14 having a ruthenium content of 2.5% based on the total weight of the catalyst, supported on silica, calcined at 275° C.) and the silica-supported ruthenium-rhodium bimetallic catalyst of Example 4 (catalyst sample E4 having a ruthenium content of 0.5 wt % and a rhodium content of 0.5 wt %, based on the total weight of the catalyst, supported on silica, calcined at 400° C.) were tested in continuous flow di-isononyl phthalate (DINP) ring hydrogenation experiments.

The continuous flow DINP hydrogenations were performed at a pressure of 80 bar (8.1 MPa) and at a temperature of 80° C. The catalyst particle size was 0.85-1.0 mm, and the weight of catalyst was 2.20 g. Liquid feed flow rate was 10 g/hr, and the feed composition was 50% DINP and 50% Isopar C as diluent. The hydrogen flow rate was 20 ml/min. Catalyst activities were calculated in first order rate constants and first order molar rate constants. The activity and selectivity of the catalysts is summarized in FIG. 9.

FIG. 9 shows the high activity of the catalyst of the invention as well as the significantly lower lights make (determined by GC analysis) than provided by the supported monometallic ruthenium catalysts.

The invention claimed is:

1. A process for ring hydrogenation of a benzenepolycarboxylic acid or derivative thereof, said process comprises the step of contacting a feed stream comprising said benzenepolycarboxylic acid or derivative thereof with a hydrogen-containing gas in the presence of a catalyst under hydrogenation conditions to produce a hydrogenated product, wherein said catalyst comprises ruthenium and rhodium applied to a support comprising from 97 to 100 wt. % silica.

2. The process of claim 1, wherein said benzenepolycarboxylic acid or derivative thereof is selected from the group consisting of $C_7$-$C_{13}$ phthalates, $C_7$-$C_{13}$ terephthalates, mixtures of $C_7$ and $C_9$ phthalates, mixtures of $C_7$ and $C_9$ terephthalates, mixtures of $C_7$ and $C_{10}$ phthalates, and mixtures of $C_7$ and $C_{10}$ terephthalates.

3. The process of claim 1, wherein said catalyst comprises ruthenium in an amount of from 0.05 to 2.5 wt. %, based on said total weight of the catalyst.

4. The process of claim 1, wherein said catalyst comprises rhodium in an amount of from 0.05 to 2.5 wt. %, based on the total weight of said catalyst.

5. The process of claim 1, wherein said catalyst comprises ruthenium and rhodium in a weight ratio of from 0.1:1 to 10:1.

6. The process of claim 1, wherein said catalyst comprises ruthenium and rhodium in a total amount of from 0.2 to 2 wt % applied to said support material which comprises silica in an amount of from 99 to 100 wt. %.

7. The process of claim 1, wherein said process is carried out at a pressure of 20 to 220 bar, a temperature of 50 to 150° C., a LVVH of from 1 to 5 $h^{-1}$ and a hydrogen excess of 50 to 200%.

8. The process of claim 1, wherein said process is carried out as a continuous process in a fixed bed reactor.

9. The process of claim 1, wherein said feed stream further comprises a diluent, wherein said diluent is present in an amount of from 50 to 200 parts per 100 parts of the benzenepolycarboxylic acid or derivative thereof.

10. The process of claim 1, wherein said feed stream further comprises water in an amount of from 0.5 to 5 wt. %, based on the total weight of the feed stream.

11. The process of claim 1, wherein said feed stream further comprises one or more isoparaffinic fluids.

12. The process of claim 1, wherein said process comprises the steps of:
a) a first hydrogenation step in which a feed stream comprising said benzenepolycarboxylic acid or derivative thereof is contacted with a first hydrogen-containing gas in the presence of a first catalyst in a first hydrogenation reactor under hydrogenation conditions to produce an at least partially hydrogenated intermediate product, wherein said first catalyst comprises a support material, and wherein said first catalyst comprises ruthenium and rhodium;
b) an intermediate product separation step, in which said at least partially hydrogenated intermediate product is separated into a first intermediate product fraction and a second intermediate product fraction;
c) a second hydrogenation step, in which said second intermediate product fraction is contacted with a second hydrogen-containing gas in the presence of a second catalyst in a second hydrogenation reactor under hydrogenation conditions to produce a hydrogenated product, wherein said second catalyst comprises a support material, and wherein said second catalyst comprises ruthenium and rhodium;
wherein said first intermediate product fraction is recycled to said first hydrogenation reactor.

13. The process of claim 12, wherein said first intermediate product fraction is recycled to said first hydrogenation reactor at a rate of 50-200% of the rate that said feed stream comprising said benzenepolycarboxylic acid or derivative thereof is fed to said first hydrogenation reactor.

14. The process of claim 12, wherein said process further comprises:
d) a product separation step, in which said hydrogenated product is separated into a first hydrogenated product fraction and a second hydrogenated product fraction;
wherein said first hydrogenated product fraction is recycled to said second hydrogenation reactor.

15. The process of claim 14, wherein said process further comprises one or more of the following steps:
i) transferring said first or second hydrogenated product to one or more reactors;

ii) separating excess hydrogen from said first or second hydrogenated product;
iii) subjecting said first or second hydrogenated product to steam stripping;
iv) drying said first or second hydrogenated product by nitrogen stripping under vacuum; and,
v) subjecting said first or second hydrogenated product to a filtration step.

16. The process of claim 14, wherein said first hydrogenated product fraction is recycled to said second hydrogenation reactor at a rate of 0-100% of the rate that said first intermediate product fraction is fed to said second hydrogenation reactor.

\* \* \* \* \*